United States Patent
Foody

(10) Patent No.: US 11,193,144 B2
(45) Date of Patent: Dec. 7, 2021

(54) PRODUCTION OF PRODUCTS WITH FAVOURABLE GHG EMISSION REDUCTIONS FROM CELLULOSIC FEEDSTOCKS

(71) Applicant: IOGEN CORPORATION, Ottawa (CA)

(72) Inventor: Patrick J. Foody, Ottawa (CA)

(73) Assignee: Iogen Corporation, Ottawa (CA)

( * ) Notice: Subject to any disclaimer, the term of this patent is extended or adjusted under 35 U.S.C. 154(b) by 287 days.

(21) Appl. No.: 16/552,622

(22) Filed: Aug. 27, 2019

(65) Prior Publication Data
US 2019/0382803 A1  Dec. 19, 2019

Related U.S. Application Data

(63) Continuation of application No. 16/284,379, filed on Feb. 25, 2019, now Pat. No. 10,428,353, which is a continuation of application No. 15/123,595, filed as application No. PCT/CA2015/050163 on Mar. 4, 2015, now Pat. No. 10,266,853, which is a continuation of application No. 14/618,170, filed on Feb. 10, 2015, now Pat. No. 9,476,066.

(60) Provisional application No. 61/948,726, filed on Mar. 6, 2014.

(51) Int. Cl.

| | |
|---|---|
| *C12P 5/02* | (2006.01) |
| *C01B 3/34* | (2006.01) |
| *C10G 45/00* | (2006.01) |
| *C12P 7/10* | (2006.01) |
| *C10G 2/00* | (2006.01) |
| *C01B 3/00* | (2006.01) |
| *C07C 1/04* | (2006.01) |
| *C10J 3/82* | (2006.01) |
| *C10L 3/08* | (2006.01) |
| *C12P 7/14* | (2006.01) |
| *C10J 3/00* | (2006.01) |

(52) U.S. Cl.
CPC ............... *C12P 5/023* (2013.01); *C01B 3/00* (2013.01); *C01B 3/34* (2013.01); *C07C 1/0485* (2013.01); *C10G 2/32* (2013.01); *C10G 45/00* (2013.01); *C10J 3/82* (2013.01); *C10L 3/08* (2013.01); *C12P 7/10* (2013.01); *C12P 7/14* (2013.01); *C01B 2203/0233* (2013.01); *C01B 2203/0244* (2013.01); *C01B 2203/0283* (2013.01); *C01B 2203/043* (2013.01); *C01B 2203/047* (2013.01); *C01B 2203/0415* (2013.01); *C01B 2203/0475* (2013.01); *C01B 2203/1211* (2013.01); *C01B 2203/1241* (2013.01); *C10J 3/00* (2013.01); *C10J 2300/0916* (2013.01); *C10J 2300/1659* (2013.01); *C10J 2300/1681* (2013.01); *C10L 2290/04* (2013.01); *C10L 2290/06* (2013.01); *C10L 2290/26* (2013.01); *C10L 2290/42* (2013.01); *Y02E 50/10* (2013.01); *Y02E 50/30* (2013.01); *Y02P 30/00* (2015.11)

(58) Field of Classification Search
CPC ..... C12P 5/023; C12P 7/10; C10J 2300/0916; C10J 2300/092
See application file for complete search history.

(56) References Cited

U.S. PATENT DOCUMENTS

| | | |
|---|---|---|
| 5,976,373 A | 11/1999 | Trocciola |
| 6,368,849 B1 | 4/2002 | Norddahl |
| 7,267,774 B2 | 9/2007 | Peyton |
| 7,883,884 B2 | 2/2011 | Bonde et al. |
| 8,153,850 B2 | 4/2012 | Hall |
| 8,231,706 B2 | 7/2012 | Gunther |
| 8,685,685 B2 | 4/2014 | Retsina et al. |
| 2004/0022698 A1 | 2/2004 | Uhrie |
| 2007/0190626 A1 | 8/2007 | Wilkening et al. |
| 2009/0032458 A1 | 2/2009 | Jensen et al. |
| 2009/0118477 A1 | 5/2009 | Hallberg et al. |

(Continued)

FOREIGN PATENT DOCUMENTS

| | | |
|---|---|---|
| CA | 2696660 | 2/2009 |
| EP | 0180670 A1 | 5/1986 |

(Continued)

OTHER PUBLICATIONS

International Search Report and Written Opinion that was issued in PCT/CA2015/050163 filed Mar. 4, 2015.

(Continued)

*Primary Examiner* — Thane Underdahl
(74) *Attorney, Agent, or Firm* — Knobbe Martens Olson & Bear LLP

(57) ABSTRACT

The present invention provides a process for producing one or more products for use as a transportation or heating fuel. In various embodiments the process comprises treating a cellulosic feedstock in one or more processing steps that release extractives from the feedstock. A solids-liquid separation is subsequently conducted on the process stream comprising the extractives and solids. An aqueous stream comprising one or more of the extractives may be fed to an anaerobic digester to produce crude biogas from which one or more impurities may optionally be removed. In various embodiments the process further comprises providing a solids stream to a thermal process. A product produced or derived from the thermal process may displace a product made from fossil fuel. One or more products obtained or derived from at least one of the foregoing process steps are provided for use as a transportation or heating fuel. In various embodiments the process enables advantaged fuel credit generation.

16 Claims, 5 Drawing Sheets

(56) References Cited

U.S. PATENT DOCUMENTS

| | | |
|---|---|---|
| 2010/0015680 A1 | 1/2010 | Van Groenestijn et al. |
| 2010/0105127 A1 | 4/2010 | Ginsburg |
| 2010/0146844 A1 | 6/2010 | Dumenil |
| 2011/0117620 A1 | 5/2011 | Rietzler |
| 2011/0226997 A1 | 9/2011 | Goruney et al. |
| 2011/0236946 A1 | 9/2011 | Maclachlan et al. |
| 2012/0058534 A1 | 3/2012 | Stover et al. |
| 2012/0094350 A1 | 4/2012 | Raap et al. |
| 2012/0094351 A1 | 4/2012 | Mahler et al. |
| 2012/0145627 A1 | 6/2012 | Benedek |
| 2013/0046479 A1 | 2/2013 | Rhodes, III |
| 2013/0089905 A1 | 4/2013 | Foody |
| 2013/0157334 A1 | 6/2013 | Van Der Heide et al. |
| 2013/0248767 A1 | 9/2013 | Ampulski et al. |

FOREIGN PATENT DOCUMENTS

| | | |
|---|---|---|
| WO | WO 2011028554 | 3/2011 |
| WO | WO 2011092136 | 8/2011 |
| WO | WO 2012088073 | 6/2012 |
| WO | WO 2012093041 | 7/2012 |
| WO | WO 2012166771 | 12/2012 |
| WO | WO 2013000088 | 1/2013 |
| WO | WO 2013029171 | 3/2013 |

OTHER PUBLICATIONS

Keith Miller "Solid-Liquid Separation Technologies in the Conversion of Bagasse to Liquid Fuel" Louisiana State University, May 2010 (May 2010), Graduate thesis.

Aden et al., "Lignocellulosic Biomass to Ethanol Process Design and Economics Utilizing Co-Current Dilute Acid Prehydrolysis and Enzymatic Hydrolysis for Corn Stover", National Renewable Energy Laboratory, NREL/TP-510-32438, Jun. 2002.

Agri-Facts, "Integrating Biogas, Confined Feedlot Operations and Ethanol Production", Alberta Agriculture and Rural Development, Agdex 768-4, Oct. 2008.

Appels et al., "Anaerobic Digestion in Global Bio-Energy Production: Potential and Research Challenges", Renewable and Sustainable Energy Reviews, vol. 15 (2011) 4295-4301.

Barakat et al., "Effect of Lignin-Derived and Furan Compounds Found in Lignocellulosic Hydrolysates on Biomethane Production", Bioresource Technology, vol. 104 (2012) 90-99.

Barta et al., "Effects of Steam Preteatment and Co-Production with Ethanol on the Energy Efficiency and Process Economics of Combined Biogas, Heat and Electricity Production from Industrial Hemp", Biotechnology for Biofuels, (2013) 6:56.

Bauer et al. "Analysis of Methane Potentials of Steam-Exploded Wheat Straw and Estimation of Energy Yields of Combined Ethanol and Methane Production", Journal of Biotechnology, vol. 142 (2009) 50-55.

Berglund et al., "Assessment of Energy Performance in the Life-Cycle of Biogas Production", Biomass and Bioenergy, vol. 30 (2006) 254-266.

Bondesson et al., "Ethanol and Biogas Production after Steam Pretreatment of Corn Stover With or Without the Addition of Sulphuric Acid", Biotechnology for Biofuels, (2013) 6:11.

Borjesson et al., "Biogas as a Resource-Efficient Vehicle Fuel", Trends in Biotechnology, vol. 26, No. 1, Jan. 2008.

California Air Resources Board, "Final Regulation Order" The unofficial electronic version of the Low Carbon Fuel Standard regulation, CleanFinalRegOrder112612.

Dererie et al., "Improved Bio-Energy Yields via Sequential Ethanol Fermentation and Biogas Digestion of Steam Exploded Oat Straw", Bioresource Technology, vol. 102 (2011) 4449-4455.

Dias et al., "Cogeneration in Integrated First and Second Generation Ethanol from Sugarcane" Chemical Engineering Research and Design, vol. 91 (2013) 1411-1417.

Humbird, "Process Design and Economics for Biochemical Conversion of Lignocellulosic Biomass to Ethanol—Dilute-Acid Pretreatment and Enzymatic Hydrolysis of Corn Stover", National Renewable Energy Laboratory, NREL/TP-5100-47764, May 2011.

Juniper, "Pyrolysis and Gasification Factsheet", Juniper Consultancy Services, 2007.

Kaparaju et al., "Bioethanol, Biohydrogen and Biogas Production from Wheat Straw in a Biorefinery Concept", Bioresource Technology 100 (2009) 2562-2568.

Kazi et al., "Techno-Economic Analysis of Biochemical Scenarios for Production of Cellulosic Ethanol", National Renewable Energy Laboratory, NREL/TP-6A2-46588, Jun. 2010.

Kemppainen et al., "Ethanol and Biogas Production from Waste Fibre and Fibre Sludge—The FibreEtOH Concept", Biomass and Bioenergy, vol. 46 (2012) 60-69.

Larsen et al., "Inbicon Makes Lignocellulosic Ethanol a Commercial Reality", Biomass and Bioenergy, vol. 46 (2012) 36-45.

Lynd et al., "How Biotech Can Transform Biofuels" Nature Biotechnology, vol. 26, No. 2 (2008), 169-172.

Maclellan et al., "Anaerobic Treatment of Lignocellulosic Material to Co-Produce Methane and Digested Fiber for Ethanol Biorefining" Bioresource Technology, vol. 130 (2013) 418-423.

Mariano et al., "Utilization of Pentoses from Sugarcane Biomass: Techno-Economics of Biogas vs. Butanol Production", Bioresource Technology, vol. 142 (2013) 390-399.

Monglia, "Enzymatic Pre-Treatment of Cellulose Rich Biomasses for Use in the Biogas Process", Thesis submitted to Department of Microbiology, Swedish University of Agricultural Sciences SLLU, ISSN 1401-5765, Jun. 2008.

Monnet, "An Introduction to Anaerobic Digestion of Organic Wastes", Final Report by Remade Scotland Initiative, Nov. 2003.

Ortiz-Gutierrez et al., "Optimal Design of Ethanol Supply Chains Considering Carbon Trading Effects and Multiple Technologies for Side-Product Exploitation", Environmental Technology, vol. 34, Nos. 13-14(2013) 2189-2199.

Pourhashem et al., "Cost and Greenhouse Gas Emission Tradeoffs of Alternative Uses of Lignin for Second Generation Ethanol", Environmental Research Letters, vol. 8 (2013) 025021.

Qiu et al., "Purification of High Strength Wastewater Originating from Bioethanol Production with Simultaneous Biogas Production", World Journal of Microbiology and Biotechnology, vol. 27 (2011) 2711-2722.

Rabelo et al., "Production of Bioethanol, Methane and Heat from Sugarcane Bagasse in a Biorefinery Concept", Bioresource Technology, vol. 102 (2011) 7887-7895.

Schausberger et al., "Modeling and Simulation of Coupled Ethanol and Biogas Production", Clean Technologies and Environmental Policy, vol. 12 (2010) 163-170.

Taherzadeh et al., "Pretreatment of Lignocellulosic Wastes to Improve Ethanol and Biogas Production: A Review", International Journal of Molecular Science, vol. 9 (2008) 1621-1651.

Tao et al., "Technoeconomic Modeling to Support the EPA Notice of Proposed Rulemaking (NOPR)", National Renewable Energy Laboratory, Technical Memorandum to National Bioenergy Center, Nov. 3, 2008.

Thamsiriroj et al., "A Roadmap for the Introduction of Gaseous Transport Fuel: A Case Study for Renewable Natural Gas in Ireland", Renewable and Sustainable Energy Reviews, vol. 15 (2011) 4642-4651.

Thamsiriroj et al., "A Critical Review of the Applicability of Biodiesel and Grass Biomethane as Biofuels to Satisfy Both Biofuel Targets and Sustainability Criteria", Applied Energy, vol. 88 (2011) 1008-1019.

Tian et al., "Anaerobic Digestion for Treatment of Stillage from Cellulosic Bioethanol Production", Bioresource Technology, vol. 144 (2013) 387-395.

Uellendahl et al., "Anaerobic Digestion as Final Step of a Cellulosic Ethanol Biorefinery: Biogas Production From Fermentation Effluent in a UASB Reactor—Pilot-Scale Results", Biotechnology and Bioengineering, vol. 107, No. 1, (2010) 59-64.

Uusitalo, V., et al.. "Economics and greenhouse gas balance of biogas use systems in the Finnish transportation sector." Renewable Energy 51 (2013): 132-140.

Verbio Vereinigte Bioenergie AG, "State-of-the-Art Technology for Making Biomethane from Agriculture Residues", Verbiogas Factsheet.

(56) References Cited

OTHER PUBLICATIONS

Zhang et al., "A Novel Full Recycling Process Through Two-Stage Anaerobic Treatment of Distillery Wastewater for Bioethanol Production from Cassava" Journal of Hazardous Materials, vol. 179 (2010) 635-641.
Zuo et al., "Soaking Pretreatment of Corn Stover for Bioethanol Production Followed by Anaerobic Digestion Process", Applied Biochemical Biotechnology, vol. 167 (2012) 2088-2102.
INBICON website, <http://www.inbicon.com/en/biomass-refinery>, configurations, access date: Dec. 9, 2014.
Patrick J. Foody, Letter addressed to Air and Radiation Docket, Environmental Protection Agency, ID No. EPA-HQ-OAR-2012-0401, Jul. 15, 2013.
Extended European Search Report dated Aug. 30, 2017 for European Patent Application No. 15758853.4.
Office Action dated Apr. 2, 2019 for European Patent Application No. 15758853.4.

PRODUCTION OF PRODUCTS WITH FAVOURABLE GHG EMISSION REDUCTIONS FROM CELLULOSIC FEEDSTOCKS

This application is a continuation of U.S. application Ser. No. 16/284,379 filed on Feb. 25, 2019, which is a continuation of U.S. application Ser. No. 15/123,595 filed Sep. 2, 2016, now U.S. Pat. No. 10,266,853, which is national stage application of PCT/CA2015/050163 having an international filing date of Mar. 4, 2015, which claims benefit of U.S. provisional Appl. No. 61/948,726 filed Mar. 6, 2014 and is a continuation of U.S. patent application Ser. No. 14/618,170 filed Feb. 10, 2015, now U.S. Pat. No. 9,476,066, each of which is hereby incorporated by reference herein.

TECHNICAL FIELD

The present invention relates to a process for producing one or more products from a cellulosic feedstock for use as transportation or heating fuel.

BACKGROUND

The majority of the energy used today is derived from fossil fuels, despite the on-going controversy surrounding their environmental impact. The extraction of fossil fuels for energy production results in the release of carbon into the atmosphere that was previously stored in the earth, and thereby has a net effect of increasing the levels of atmospheric $CO_2$. On the other hand, $CO_2$ released from combusting cellulosic feedstock is relatively benign, given that it simply returns to the atmosphere carbon that was previously removed therefrom by plant photosynthesis. Displacing fossil-based fuel with biomass derived fuel creates greenhouse gas (GHG) benefits by displacing $CO_2$ emissions that would have been from the fossil fuel. Various governments have promoted the increased use of renewable fuel through legislative and regulatory regimes, including the Energy Independence and Security Act (EISA) in the United States.

Although the use of cellulosic feedstocks to produce biofuels is known to have the potential to reduce GHG emissions from the fossil fuel industry, this has proven to be difficult to achieve in practice due to economic and technical challenges. Despite much effort and research on producing energy from renewable energy sources, non-fossil fuel options are still in their infancy. Thus, there is a need in the art for new sources of energy that are more environmentally benign than fossil fuels and that overcome some of the economic and technical challenges inherent in known processes for utilizing the energy from cellulosic feedstock.

Biogas is a biofuel produced by anaerobic digestion that has been receiving increased attention in recent years. Biogas contains predominantly methane and is commonly used as heating fuel or for electricity generation, although it can potentially also be used as a transportation fuel or as an intermediate to produce another fuel. A benefit of making biogas is that a wide variety of feedstocks can be used to produce the gas, including landfill waste or waste streams from commercial plants. In the production of ethanol from cellulosic feedstocks, waste streams remaining after the recovery of ethanol are often treated by anaerobic digestion to produce biogas. Landfills also produce biogas through anaerobic digestion of municipal waste. While the biogas is commonly used on-site for heating or electricity generation, for example at a plant or a landfill site, its use is less widespread in the transportation sector. However, commercializing the use of biogas in other applications besides on-site use at a plant or other facility would be desirable.

Biofuel can also be produced from cellulosic feedstock by thermal processes such as gasification. Gasification includes processes in which cellulosic feedstock is subjected to high temperatures to make syngas comprising hydrogen and carbon monoxide and optionally other components such as carbon dioxide, methane and water. The gasification step to produce syngas is generally carried out above 500° C. up to 1500° C. The syngas in turn can be used as an intermediate to produce other fuels. For example, to generate methane from the syngas, a methanation reaction of syngas is conducted to produce a fuel comprised primarily of methane. Other thermal processing of cellulosic feedstock, such as pyrolysis and combustion, can be used to produce biofuels such as pyrolysis oil or other energy products, including electricity and heat as described herein.

However, the thermal processing of streams from cellulosic feedstock, including combustion, gasification and/or pyrolysis, can be hindered by the presence of various extractives present in cellulosic feedstock. Such extractives include inorganic salt, silica, pentose sugars, hexose sugars and/or organic acids, which may produce slag, pollutants and other undesirable components during thermal processing. Inorganic salt can be particularly problematic as it can form a low melting material produced by the combination of silica with alkali salts. This low melting point material can lead to fouling of boilers or gasification units, requiring shut-downs and expensive cleaning. Extractives can also contribute to problematic tars in gasification operations.

There is thus a need in the art to overcome some of the challenges of making fuels, fuel intermediates and/or energy products from cellulosic feedstock, particularly biogas and products from thermal processes. A process for improving the efficiency of such processes while maintaining a beneficial GHG emission impact could meet this need.

SUMMARY OF THE INVENTION

According to one aspect, the present invention enables the production of a fuel from cellulosic feedstock with favourable GHG emission reductions and that overcomes some of the limitations of known processes for utilizing energy and making products from such feedstocks.

Embodiments of the invention improve the thermal processing of cellulosic feedstock, including combustion, gasification and/or pyrolysis by releasing various extractives present in cellulosic feedstock, which present problems such as the production of slag, pollutants and other undesirable components during thermal processing. By removing these released extractives during processing by a solids-liquid separation, a solids stream is obtained with improved characteristics for use in a thermal process, which in turn may improve the economics of producing energy products from the cellulosic feedstock. Thus, embodiments of the present invention provide one or more products derived from cellulosic feedstock from which energy from a thermal process can be more economically captured.

The solids-liquid separation provides additional benefits. According to certain embodiments of the invention, an aqueous stream from the solids-liquid separation comprising the extractives removed from the feedstock is fed to anaerobic digestion to produce biogas. The biogas or one or more products derived therefrom can be provided for use as a transportation or heating fuel via an apparatus for transporting methane, such as a pipeline or shipping container.

Carrying out a solids-liquid separation in advance of anaerobic digestion enables microorganism recycle in an anaerobic digester, which can improve the productivity of the anaerobic digestion due to the higher microbe concentration in the digester. Further, removing solids before anaerobic digestion simplifies the process since the presence of solids in anaerobic digestion can make solids-liquid separation more difficult or lead to higher water containing solids streams. Moreover, because the separation is conducted without microbes, it can be carried out with greater ease and at lower cost compared to a process in which the separation is conducted after the anaerobic digestion. In addition, the absence of solids in anaerobic digestion can permit different reactor designs that could not otherwise be employed with solids present resulting in higher productivity or higher cost. Yet a further potential benefit of the solids-liquid separation is that streams downstream of the anaerobic digester can be more concentrated, which can reduce the cost of their disposition.

Embodiments of the invention also enable improved processes for recycling liquid streams. In one embodiment of the invention, a liquid stream originating from the anaerobic digester that comprises inorganic salt is introduced back to the digester itself or to any stage upstream of the digester, but that is downstream from a stage of the process that releases extractives, such as a pretreatment step. Such a pretreatment step typically involves the use of pretreatment chemical, such as acid or base, to make the feedstock more amenable to a subsequent step of enzymatic hydrolysis or other process step. By introducing such a salt-containing stream to a stage downstream of pretreatment, less salt is introduced to pretreatment. Introducing less salt in turn avoids buffering effects due to the salt, which may reduce the amount of chemical required during the pretreatment to adjust the pH of the feedstock.

The salt-containing stream may then be purged. By the term "purging", it is meant that the salt-containing stream is split into a main stream and a purge stream that is separated or withdrawn from the main stream. Such purge stream typically has a higher concentration of inorganic salts than organics. The purged stream may be re-used in the process to neutralize acid, used off-site or provided for use as a vendible product, such as a fertilizer. Thus, such embodiment not only allows for reductions in water usage, but also provides a salt-containing stream that finds use in various applications.

The purge stream may be subjected to a water removal step to produce a concentrated salt stream. Advantageously, removing water from the purge stream is more energy efficient than water removal from the complete salt-containing stream withdrawn from the digester, which can lead to GHG reductions as described herein. The removed water can optionally be recycled in the process. A concentrated inorganic salt-containing stream from which the water has been removed can then be processed more readily. For example, the concentrated stream can be more easily disposed of or inorganic salt can be more readily recovered therefrom for use as fertilizer or the concentrated stream can be re-used in the process to at least partially neutralize acid, as described herein.

Another embodiment of the invention involves obtaining a condensate stream from the process and introducing at least a portion of such stream to the process to reduce water usage. The introduction of a process condensate may increase the concentration of acetic acid, acetate, or a combination thereof, in the anaerobic digestion, which in turn may increase the yield of biogas. Moreover, the process condensate will contain a lowered concentration of non-volatile components, such as inorganic salts. Because such stream has reduced salt concentration, it is particularly suitable for introduction to pretreatment or upstream of a pretreatment step to reduce water usage.

For example, the purge stream may be subjected to a water removal step that includes evaporation and the condensate subsequently used in the process to reduce water usage. Due to its low salt concentration, the stage of the process in which the condensate is introduced may include an upstream stage of the process such as pretreatment.

In addition, embodiments of the present invention provide for fuel credit generation. The extractives fed to the anaerobic digester can improve renewable fuel yield from cellulosic feedstock, which is especially beneficial in that it can enable generation of a greater number of fuel credits. The process of the invention also provides products produced or derived from the foregoing process steps that possess significantly reduced life cycle GHG emissions relative to a gasoline baseline, which further enables advantaged fuel credit generation. Thus, conducting a solids-liquid separation prior to anaerobic digestion may not only improve the economics of energy capture from cellulosic feedstock, but also provide a mechanism for improving the prospects of the process for commercialization through fuel credit generation.

According to a first aspect of the invention, there is provided a process for producing a transportation or heating fuel comprising the steps of: (i) treating a cellulosic feedstock in one or more processing steps that release extractives comprising at least acetic acid, acetate, or a combination thereof from the feedstock; (ii) conducting a solids-liquid separation on a process stream comprising the extractives and solids, thereby producing an aqueous stream comprising at least a portion of the extractives and a solids stream comprising insoluble components; (iii) feeding at least a portion of the aqueous stream to an anaerobic digester to produce a crude biogas that comprises carbon dioxide; (iv) removing at least 80 weight % of the carbon dioxide present in the crude biogas to produce a purified biogas; (v) providing an inorganic salt-containing liquid stream originating from the anaerobic digester and introducing at least a portion of the inorganic salt-containing liquid stream to (a) the anaerobic digester; (b) a stage upstream of the anaerobic digester; or (c) a combination thereof; (vi) purging a stream comprising inorganic salt from said inorganic salt-containing liquid stream; (vii) providing solids from at least one stream selected from the solids stream comprising the insoluble components and a second solids stream comprising insoluble components to a thermal process to produce an energy product; (viii) introducing the purified biogas produced in step (iv) to a pipeline and causing withdrawal of an amount of methane from said pipeline corresponding to an amount of the purified biogas introduced to the pipeline; (ix) providing one or more products obtained or derived from step (vii), step (viii), or a combination thereof, for use as a transportation or heating fuel; and (x) generating or causing the generation of a renewable fuel credit.

Optionally, the salt-containing liquid stream of step (v) of the foregoing aspect of the invention is introduced to a stage upstream of the anaerobic digester and downstream of step (i). According to another embodiment of the above aspect of the invention, a purge stream produced from the step of purging is subjected to further processing, such as a water removal step.

According to a further aspect of the invention, there is provided a process for producing a transportation or heating fuel comprising the steps of: (i) treating a cellulosic feedstock in one or more processing steps that release at least acetic acid, acetate, or a combination thereof from the feedstock; (ii) conducting a solids-liquid separation on a process stream comprising at least the acetic acid, acetate, or a combination thereof and solids comprising insoluble components, thereby producing an aqueous stream comprising at least a portion of the acetic acid, acetate, or a combination thereof, and a solids stream comprising the insoluble components; (iii) feeding the aqueous stream or a portion thereof comprising the acetic acid, acetate or a combination thereof, to an anaerobic digester to produce crude biogas that comprises carbon dioxide; (iv) removing at least 80 weight percent of the carbon dioxide present in the crude biogas to produce a purified biogas; (v) providing solids from at least one stream selected from the solids stream comprising the insoluble components and a second solids stream comprising insoluble components to a thermal process to produce an energy product; (vi) introducing the purified biogas produced in step (iv) to a pipeline and causing withdrawal of an amount of methane from said pipeline corresponding to an amount of the purified biogas introduced to the pipeline; (vii) providing one or more products obtained or derived from step (iv), step (v), or a combination thereof, for use as the transportation or heating fuel, wherein the transportation or heating fuel has GHG emissions associated therewith that are at least 50% lower than a gasoline baseline as determined by EPA methodology; and (viii) generating or causing generation of a renewable fuel credit.

According to a further aspect of the invention, there is provided a process for producing a transportation or heating fuel comprising the steps of: (i) treating a cellulosic feedstock in one or more processing steps that release at least acetic acid, acetate, or a combination thereof from the feedstock; (ii) conducting a solids-liquid separation on a process stream comprising at least the acetic acid, acetate, or a combination thereof and solids comprising insoluble components, thereby producing an aqueous stream comprising at least the acetic acid, acetate, or a combination thereof, and a solids stream comprising the insoluble components; (iii) feeding the aqueous stream or a portion thereof comprising the acetic acid, acetate, or a combination thereof to an anaerobic digester to produce a crude biogas that comprises carbon dioxide; (iv) removing at least 80 weight percent of the carbon dioxide present in the crude biogas to produce a purified biogas; (v) providing a condensate stream from the process and introducing at least a portion of the condensate stream to the anaerobic digester, a step upstream of the digester or a combination thereof; (vi) providing solids from at least one stream selected from the solids stream comprising the insoluble components and a second solids stream comprising insoluble components to a thermal process to produce an energy product; (vii) introducing the purified biogas produced in step (iv) to a pipeline and causing withdrawal of an amount of methane from said pipeline corresponding to an amount of the purified biogas introduced to the pipeline; (viii) providing one or more products obtained or derived from step (vi), step (vii), or a combination thereof, for use as a transportation or heating fuel; and (ix) generating or causing generation of numerical information relating to the one or more products of step (viii), said information comprising at least 1 parameter selected from: (a) the type of transportation or heating fuel; (b) the year in which the product was produced; (c) a registration number associated with the producer or importer; (d) a serial number associated with a batch; and (e) an amount of fuel used as a fossil fuel replacement.

According to a further aspect of the invention, there is provided a process for producing a transportation or heating fuel comprising the steps of: (i) treating a cellulosic feedstock in one or more processing steps that release extractives comprising acetic acid, acetate or a combination thereof from the feedstock; (ii) conducting a solids-liquid separation on a process stream comprising the extractives and solids, thereby producing an aqueous stream comprising the extractives and a solids stream comprising insoluble components; (iii) feeding at least a portion of the aqueous stream comprising one or more of the extractives to an anaerobic digester to produce a crude biogas that comprises carbon dioxide; (iv) removing at least 80 wt % of the carbon dioxide present in the crude biogas to produce a purified biogas; (v) carrying out or causing one or more parties to carry out a process comprising (a) gasifying solids from at least one stream selected from the solids stream comprising the insoluble components and a second solids stream comprising insoluble components to produce syngas, and (b) reacting the syngas to form a fuel or fuel intermediate; (vi) introducing the purified biogas produced in step (iv) to a pipeline and causing withdrawal of an amount of methane from said pipeline corresponding to an amount of the purified biogas introduced to the pipeline; (vii) providing one or more products obtained or derived from step (v), step (vi) or a combination thereof for use as a transportation or heating fuel; and (viii) generating or causing generation of a renewable fuel credit with respect to said one or more products.

According to an embodiment of any of the foregoing aspects of the invention, the one or more products produced from any of the foregoing aspects of the invention are derived from the methane withdrawn from the pipeline.

In various embodiments of any of the foregoing aspects of the invention, the cellulosic feedstock is straw, stover or an energy crop.

According to an embodiment of any of the foregoing aspects of the invention, the process comprises removing additional liquid from the solids stream of step (ii) to produce a concentrated solids stream.

In a further embodiment of any of the foregoing aspects of the invention, at least a portion of the inorganic salt-containing liquid stream of step (v) is introduced to the solids-liquid separation.

Embodiments of any of the above aspects of the invention further comprise conducting a second solids-liquid separation on the solids stream comprising the insoluble components or a stream derived therefrom to produce a second aqueous stream and introducing the second aqueous stream or a portion thereof to the digester or to a stage upstream of the digester.

Embodiments of any of the above aspects of the invention further comprise obtaining a slurry comprising microorganisms from the digester, conducting a solids-liquid separation on the slurry to obtain a concentrated slurry of microorganisms and introducing the concentrated slurry of microorganisms to the digester or to a stage upstream of the digester. The solids stream of step (vii) may be gasified in the thermal process to produce syngas and the syngas reacted to form methane.

In further embodiments of any of the above aspects of the invention, the aqueous stream of step (ii) comprises sulfur and the process further comprises: (a) converting the sulfur or a portion thereof to gaseous hydrogen sulfide in said digester; (b) treating the gaseous hydrogen sulfide to produce elemental sulfur or an oxide of sulfur; (c) recovering an acid comprising sulfuric acid, sulfurous acid, sulfur dioxide or a combination thereof from the elemental sulfur or oxides of sulfur; and (d) using the recovered acid in the process as a catalyst or for neutralizing alkali.

DETAILED DESCRIPTION OF THE INVENTION

Feedstock

Figure 1:
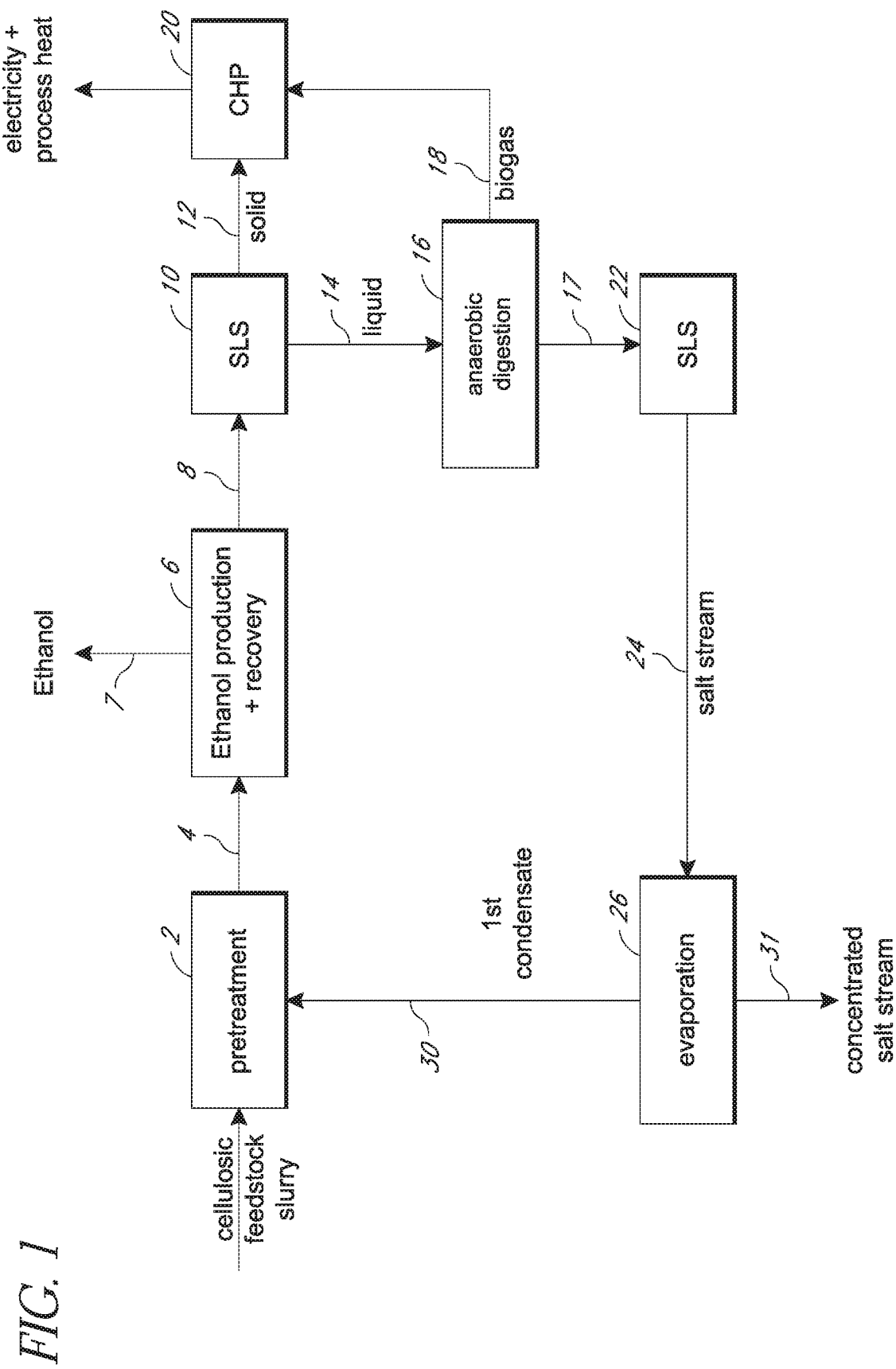
FIG. 1 is a description of a comparative process to illustrate certain advantageous features of embodiments of the invention.

Embodiments of the process of the invention utilize a cellulosic feedstock. By the term "cellulosic feedstock", it is meant any type of woody or non-woody plant biomass, or feedstock derived from plant biomass. The combined content of cellulose, hemicellulose and lignin in the cellulosic feedstock is typically greater than 25 wt % (w/w). Sucrose, fructose and starch can be present, but usually in lesser amounts than cellulose and hemicellulose.

Examples of cellulosic feedstock are known to those skilled in the art and include (i) energy crops; (ii) residues, byproducts or waste from the processing of plant biomass in a facility, or feedstock derived therefrom; (iii) agricultural residues; (iv) forestry biomass; (v) waste material derived from pulp and paper products; (vi) pulp and paper waste; and/or (vii) municipal waste including components removed from municipal waste.

Energy crops include biomass crops such as grasses, including C4 grasses, such as switch grass, energy cane, sorghum, cord grass, rye grass, *miscanthus*, reed canary grass, C3 grasses such as *Arundo donax* or a combination thereof.

Residues, byproducts or waste from the processing of plant biomass in a facility or feedstock derived therefrom include residues remaining after obtaining sugar from plant biomass such as sugar cane bagasse, sugar cane tops and leaves, beet pulp, or residues remaining after removing sugar from Jerusalem artichoke or residues remaining after grain processing, such as corn fiber, corn stover or bran from grains. Agricultural residues include, but are not limited to soybean stover, corn stover, rice straw, sugar cane tops and/or leaves, rice hulls, barley straw, corn cobs, wheat straw, canola straw, oat straw, oat hulls, corn fiber or corn cobs.

Forestry biomass includes recycled wood pulp fiber, sawdust, hardwood, softwood, trimmings and/or slash from logging operations. Pulp and paper waste, includes waste from chemical pulping such as black liquor, spent sulfite liquor, sludge, fines and/or precipitated lignin.

Municipal waste includes post-consumer material or waste from a variety of sources, such as domestic, commercial, institutional and/or industrial sources. For example, the term includes refuse from waste collection and/or sewage sludge.

Cellulosic feedstock can be a mixture of fibers that originate from different kinds of plant materials, including mixtures of cellulosic and non-cellulosic feedstocks. In addition, the cellulosic feedstock may comprise fresh cellulosic feedstock, partially dried cellulosic feedstock, fully dried cellulosic feedstock, or a combination thereof. Moreover, new cellulosic feedstock varieties may be produced from any of those listed above by plant breeding or by genetic engineering.

In an embodiment of the invention, the cellulosic feedstock is a non-woody feedstock such as (i) an energy crop, (ii) residues, byproducts or waste from the processing of plant biomass or feedstock derived therefrom in a facility, and/or (iii) agricultural residues. In another embodiment of the invention, the cellulosic feedstock is straw, stover or an energy crop. As used herein, straw refers to the stem, stalk and/or foliage portion of crops remaining after the removal of starch and/or sugar containing components for consumption. Examples of straw include, but are not limited to sugar cane tops and/or leaves, oat straw, wheat straw, rye straw, oat straw, rice straw and barley straw. Stover includes the stalk and foliage portion of crops after the removal of starch and/or sugar containing components of plant material for consumption. Examples of stover include, but are not limited to soybean stover, sorghum stover and corn stover.

Non-woody feedstocks generally contain higher levels of ash than woody feedstocks. Such non-woody feedstocks will contain greater than 0.5 wt % ash (w/w), greater than 1 wt % ash (w/w), or more typically greater than 3 wt % (w/w) ash. The ash includes, but is not limited to, silica, and salts of potassium, calcium and sodium. In certain embodiments of the invention, the ash content of the non-woody cellulosic feedstock is between about 0.5 wt % and about 18 wt %, between about 1 wt % and about 17 wt %, between about 2 wt % and about 17 wt %, between about 3 wt % and about 17 wt % or between about 3.5 wt % and about 16 wt % (w/w). The amount of ash is expressed as the percentage of residue remaining after dry oxidation at 575° C. in accordance with NREL Technical Report NREL/TP-510-42622, January 2008, which is incorporated herein by reference. The results are reported relative to a 105° C. oven dried sample (dried overnight).

Without being limiting in any manner, the cellulosic feedstock may be slurried prior to or during the step of releasing extractives. In a further embodiment, the cellulosic feedstock is not slurried but rather contacted with liquid with or without any feedstock size reduction.

If slurrying is conducted, it may be carried out in any batch or continuous mixing vessel at any desired consistency. In an embodiment of the invention, the undissolved solids content of the slurry or other process stream containing undissolved solids is between about 1 and about 30 wt % (w/w). The undissolved solids content is a weight ratio of dry solids to liquid in a process stream, and is arrived at by determining the weight of a sample and then filtering the sample through filter paper and washing with water to isolate the undissolved solids. The isolated, undissolved solids are dried overnight at 105° C., preferably in an aluminum drying dish, and then weighed. The undissolved solids content is quantified by determining the number of grams of dry solids per gram of process stream or other solution and expressing the result as a percentage.

Releasing Extractives

In various embodiments the process of the invention comprises treating a cellulosic feedstock so as to release extractives. By "release extractives" it is meant contacting the feedstock with an aqueous solution in one or more liquid processing steps to remove one or more extractives so that they become part of the soluble component of an aqueous medium, while insoluble components remain. The feedstock that is contacted with the aqueous solution may have been previously subjected to one or more prior processing steps, including heat treatment, mechanical processing, addition of one or more chemicals or catalysts, or combinations thereof. Extractives may also be released from a feedstock that has not been subjected to such prior processing step(s). In an embodiment of the invention, at least about 5 wt %, about 10 wt % or about 15 wt % (w/w) of insoluble components remain after processing steps to release extractives as measured by dry weight. In a further embodiment, between about 5 wt % and about 90 wt %, or between about 10 wt % and about 80 wt %, or between 40 wt % and 80 wt %, or between about 10 wt % and 50 wt %, or between 10 wt % and 60 wt % or between 10 wt % and 40 wt % (w/w) of extractives are removed as measured by weight of the original cellulosic feedstock.

Extractives include components that become part of an aqueous medium after processing steps that include application of heat, mechanical energy, chemicals, catalysts or a combination thereof. The catalysts may be chemical or biological. Examples of extractives include sugar, inorganic salt, organic acid, organic salt, byproducts of the process, such as degradation products and fermentation byproducts, protein, soluble lignin, pectin, or a combination thereof.

The sugar includes sugar monomers, oligomers comprising two or more sugar monomers, sugar polymers and combinations thereof. Examples of sugars include hemicellulose, polymers or oligomers of six carbon sugars, polymers or oligomers of five carbon sugars and monomers of six and five carbon sugars.

Examples of inorganic salt include potassium, calcium and sodium salts. Other salts that may be removed are magnesium, manganese and iron. The salts may be present as sulfate salts, phosphate salts, chloride salts, bromide salts, glycolate salts, trifluoro acetate salts and/or oxalate salts. In an embodiment of the invention, the inorganic salts comprise at least potassium. The level of inorganic salt removed may be 0.5 wt % to 10 wt % or 1 wt % to 8 wt % (w/w) as measured by weight of the cellulosic feedstock prior to the one or more processing steps. Determination of the amount of inorganic salt involves measuring residue remaining after dry oxidation as described above in connection with ash determination before and after the one or more processing steps to remove extractives.

Examples of organic acids include acetic acid, galacturonic acid, formic acid, glucuronic acid and a combination thereof. Organic salts may include acetate, galacturonate, formate, glucuronate and a combination thereof. Byproducts include degradation products such as furfural, hydroxymethylfurfural (HMF) and furans, and/or fermentation byproducts such as lactic acid and glycerol.

In one embodiment of the invention, between 10 and 100 wt %, or between 20 and 100 wt % (w/w), of the insoluble component of the cellulosic feedstock is retained after the one or more processing steps.

At least a portion of the lignin, if such component is present, is typically retained when removing extractives, although a certain amount may become soluble. Between 1 and 90 wt % (w/w) of the lignin may become dissolved during the one or more processing steps. For example, dissolution of lignin may occur during an alkaline conditioning carried out prior to a pretreatment (see WO 2012/019305) or during a pretreatment process, as discussed below. A further non-limiting example of a pretreatment that dissolves a portion of the lignin is sulfur dioxide pretreatment.

The weight ratio of water-to-feedstock (wt:wt) fed to the one or more processing steps that release extractives may be 0.5:1 to 25:1, 0.5:1 to 20:1, 0.5:1 to 15:1, 0.5:1 to 10:1, or 0.5:1 to 5:1 as determined relative to the original cellulosic feedstock.

The one or more processing steps that release extractives may be catalyzed or uncatalyzed, and conducted with or without heat treatment. Such steps may include one or more pretreatments, meaning a step in which cellulosic feedstock is reacted under conditions that disrupt the fiber structure and that increase the susceptibility or accessibility of cellulose within the cellulosic fibers for a subsequent treatment. Non-limiting examples of pretreatment and optional preliminary treatments are described further below.

A preliminary treatment step can be a pre-conditioning step, which is a step used to prepare a feedstock for pretreatment. Examples of pre-conditioning include (i) leaching, (ii) chemical treatment, including but not limited to alkali treatment, swelling or soaking, (iii) heat treatment, or a combination thereof.

Leaching is a process in which feedstock, either with or without size reduction, is contacted with a liquid to remove one or more extractives. Contacting with the liquid may be carried out by washing, spraying and the like. In an embodiment, the liquid is water which leaches inorganic salts and other soluble components present in the feedstock into the resulting aqueous medium or leachate. The insoluble components are subsequently separated from the leachate in a solids-liquid separation (SLS) and a resulting process stream comprising the salts is sent to anaerobic digestion.

Chemical treatment prior to pretreatment may involve the use of an alkali treatment to remove acetyl groups; swelling with alkali or soaking with acid. The chemical treatment may include chemical processes to solubilize or extract lignin, an example of which includes chemical pulping.

Heat treatment may include the use of heat to treat the feedstock at a temperature of above 80° C. This can involve a step of steaming or a soaking step with application of heat. The feedstock may be heated with steam using commercially available mixing devices designed for introducing steam and optionally chemical through spray nozzles.

After the optional preliminary treatment step, the feedstock may be subjected to pretreatment. Pretreatment can be with heat, mechanical processing, addition of one or more chemicals, biocatalysts, or combinations thereof to release salts and/or solubilize components of the feedstock, such as sugars. Pretreatment can be carried out with washing or leaching to remove soluble components as they are solubilized. After pretreatment, between 30 and 100 wt % of the xylan may be hydrolyzed, although there may be limited xylan hydrolysis during some pretreatments. After pretreatment, between 10 and 100 wt % of the lignin may remain insoluble.

Non-limiting examples of pretreatment include acid pretreatment, alkali pretreatment and hydrothermal pretreatment, each of which are discussed in turn below.

An acid pretreatment may be carried out at a maximum temperature of about 120° C. to about 280° C. The acid may be selected from sulfuric acid, sulfurous acid, sulfur dioxide, phosphoric acid and/or hydrochloric acid. The time that the feedstock is held at this temperature may be in the range of about 6 seconds to about 2 hours. The acid pretreatment produces a composition comprising an acid pretreated feedstock. Sugars produced by the hydrolysis of hemicellulose during acid pretreatment are generally present in the composition and include xylose, glucose, arabinose, mannose, galactose or a combination thereof. Organic acids may be present in the composition as well and may include acetic acid, galacturonic acid, formic acid, lactic acid, glucuronic acid or a combination thereof. Many cellulosic feedstocks contain hemicellulose with acetyl groups attached to xylan. Pretreatment processes typically liberate acetic acid from the acetyl groups.

Examples of suitable alkaline pretreatment processes include ammonia fiber expansion (AFEX) or dilute ammonia pretreatment. According to the AFEX process, the cellulosic feedstock is contacted with ammonia or ammonium hydroxide, which is typically concentrated, in a pressure vessel. The contact is maintained for a sufficient time to enable the ammonia or ammonium hydroxide to swell the cellulose fibers. The pressure is then rapidly reduced which allows the ammonia to flash or boil and disrupt the cellulose fiber structure. The flashed ammonia may then be recovered according to known processes. The AFEX process may be run at about 20° C. to about 150° C. or at about 20° C. to about 100° C. and all temperatures therebetween. The duration of this pretreatment may be about 1 minute to about 20 minutes, or any time therebetween.

Dilute ammonia pretreatment utilizes more dilute solutions of ammonia or ammonium hydroxide than AFEX. Such a pretreatment process may or may not produce any monosaccharides. Dilute ammonia pretreatment may be conducted at a temperature of about 100 to about 150° C. or any temperature therebetween. The duration for such a pretreatment may be about 1 minute to about 20 minutes, or any time therebetween.

A hydrothermal pretreatment can be carried out without the addition of pretreatment chemical, with the application of heat. An example of a suitable temperature for hydrothermal pretreatment is between about 80° C. and about 400° C., between about 80° C. and about 260° C., or between about 100° C. and about 210° C. Without being limiting, an extruder is an example of equipment that can be used to carry out hydrothermal pretreatment. An example of hydrothermal pretreatment includes the application of heat to hydrolyze acetyl groups in the feedstock. A further example is hydrothermal carbonization of cellulosic feedstock in pressurized liquid at elevated temperatures, such as between 150° C. and 370° C., typically without oxygen or low levels thereof. Hydrothermal carbonization produces a material known as "hydrochar", which is a carbon-containing product that is typically solid having improved properties for gasification.

Optionally, the foregoing processing steps are conducted as part of a cellulosic conversion process to produce a fuel or chemical, such as an alcohol. Such a conversion process may include pretreating a cellulosic feedstock to disrupt fiber structure and improve accessibility of cellulose to a subsequent enzymatic or chemical treatment, enzymatic or chemical hydrolysis to hydrolyze cellulose to glucose, fermentation of glucose to a product and optionally concentration of the product by distillation. Enzymes may include cellulases, hemicellulases, amylases, glucanases, proteases, lipases, pectinases, laccases, phytases or combinations thereof.

Solids-Liquid Separation

Embodiments of the process of the invention comprise conducting one or more solids-liquid separations on one or more process streams comprising extractives and solids. In some embodiments the solids comprise insoluble components derived from the feedstock, which may comprise lignin. The solids-liquid separation produces a solids stream and an aqueous stream comprising at least a portion of the extractives. In various embodiments the aqueous stream comprising the extractives is sent to anaerobic digestion, while the solids stream is provided to a thermal process, e.g., as discussed further below.

Conducting the solids-liquid separation prior to anaerobic digestion is advantageous in that it permits downstream cell recycle, which in turn can improve the productivity of the anaerobic digestion by re-introducing a stream comprising microbes into the digester, thereby resulting in a higher microbe concentration in the digester. A further advantage of conducting a solids-liquid separation prior to anaerobic digestion is that it enables the use of a wider range of reactor types. For example, certain reactors are prone to plugging by solids, particularly a reactor type known as a packed bed reactor. Removal of solids prior to anaerobic digestion can reduce or eliminate plugging in these types of reactors, which in turn requires fewer tanks, improves conversion and thus results in improved productivity.

The process stream comprising the extractives and solids that is introduced to the solids-liquid separation can be any stream resulting from the one or more processing steps that release extractives from the feedstock. In a non-limiting embodiment of the invention, the process stream is a slurry. According to such embodiment, the undissolved solids content of the process stream fed to solids-liquid separation can be between 1 and 30 wt % or between 2 and 25 wt % (w/w). As mentioned, the process stream comprising the extractives and solids need not be derived from a slurried feedstock. The process stream may be a feedstock in aqueous solution resulting from applying liquid to a feedstock without prior slurrying. In such embodiment, the liquid is present at a weight ratio of 0.5:1 to 0.5:30 parts liquid per part feedstock (wt:wt). A non-limiting example of such a liquid processing step is leaching. In this embodiment, the solids-liquid separation may be integrated within the leaching process itself or carried out after leaching.

When the one or more processing steps are part of a cellulosic conversion process to produce a fuel or chemical which involves a product recovery step such as distillation, or other technique to concentrate a product, the solids-liquid separation may be upstream, downstream or both upstream and downstream of the product recovery step. In an embodiment of the invention, the product recovery such as a distillation is downstream of the solids-liquid separation. When the product recovery is downstream of the solids-liquid separation, the process stream fed to the solids-liquid separation may be a liquid stream comprising solids containing leached or conditioned feedstock, a liquid stream comprising pretreated feedstock solids, a stream remaining after an enzymatic hydrolysis, a stream comprising fermented beer after fermentation or a combination thereof.

It should be understood that the solids-liquid separation is any process in which liquid is removed from the process stream comprising the extractives and solids, thereby removing at least a portion of the extractives from insoluble components. In an embodiment, substantially all of the extractives are separated from the solids by the solids-liquid separation. The solids-liquid separation may include mechanical methods such as centrifugation, filtering, pressing, including pressing that employs a screw or nip press, draining or sedimentation; chemical methods, such as the addition of flocculating agents; and/or thermal methods to remove water, such as evaporation, drying, flashing and/or distillation. The filtering may include microfiltration, plate and frame filtration, cross-flow filtration, pressure filtration and/or vacuum filtration. Further, the solids-liquid separation can include a washing step within the separation.

The solids-liquid separation produces a solids stream and an aqueous stream comprising one or more of the extractives. The solids stream may comprise lignin and optionally other undissolved components such as cellulose, xylan or a combination thereof. In an embodiment of the invention, the solids stream comprises at least lignin and cellulose. The undissolved solids content of the solids stream can be between 5 and 70 wt %, or between 20 and 50 wt % (w/w).

Examples of extractives in the aqueous stream resulting from the solids-liquid separation include sugar, inorganic salt, organic acid, byproducts of the process, such as degradation products and fermentation byproducts, protein, soluble lignin, pectin, or a combination thereof. In an embodiment, the aqueous stream from the solids-liquid separation comprises at least sugars from a pretreatment, such as xylose, glucose, galactose, mannose, arabinose or a combination thereof. In a further embodiment, the aqueous stream comprises at least inorganic salts, salts of organic acids and/or organic acids.

In an embodiment of the invention, the aqueous stream comprising the extractives comprises at least acetic acid, acetate or a combination thereof. Acetic acid, acetate or a combination thereof may be liberated during a pretreatment and arise from hemicellulose that contains acetyl groups attached to xylan. Without being limiting, the acetate may be a salt of potassium or sodium. While acetic acid and/or acetate can inhibit yeast and enzymes used in the process, the presence of one or more of these chemical species in anaerobic digestion typically does not substantially inhibit the microbes in the anaerobic digester. Thus, in certain embodiments, the acetic acid and/or acetate need not be removed from the aqueous stream when it is fed to the anaerobic digester. This in turn can simplify and reduce the costs of the process as processes for removal of acetic acid and/or acetate from streams are often complicated and costly. A further advantage is that feeding acetic acid and/or acetate to the anaerobic digester can increase the amount of biogas produced, or a product derived therefrom, which in turn can provide a higher yield of fuel credits per unit of feedstock, thereby providing incentives for commercializing the process.

The concentration of acetic acid and/or acetate in the aqueous stream comprising the extractives may be between 0.1 and 120 g/L or between 5 and 100 g/L or between 5 and 50 g/L or between 5 and 40 g/L. As would be appreciated by those of skill in the art, the molecular species present in solution will depend on the pH. Thus, the concentration ranges represent the combined amount of acetate and acetic acid species present in solution.

Anaerobic Digestion

The aqueous stream comprising the extractives is subsequently fed to an anaerobic digester to produce crude biogas, although it will be appreciated that, prior to feeding the aqueous stream to anaerobic digestion, one or more processing steps may be conducted on the aqueous stream.

By "anaerobic digester", it is meant a tank, or other contained volume, such as a covered lagoon, designed to facilitate the breakdown of organic material in the aqueous stream by microorganisms under anaerobic or low oxygen conditions. The anaerobic digestion may be carried out in one or multiple anaerobic digesters connected in series, parallel or a combination thereof. Thus, the anaerobic digester may be one of a plurality of fluidly connected digesters.

An anaerobic digester utilized in accordance with the invention may be designed and/or operated in a number of configurations including batch or continuous, mesophilic or thermophilic temperature ranges, and low, medium or high rates. The rate refers to the reduction (or digestion) of chemical oxygen demand (COD) per unit of volume to the unit, which is a rate measurement based on the removal of organic compounds present in the feed. In practice, the configuration utilized will depend on a number of factors. These may include consideration of the nature of the organic material in the aqueous stream to be treated and/or the level of treatment desired. Other factors that may be considered in the configuration choice include operating parameters such as residence time, temperature, pH and the nutrients supplied to a digester. Design choices also include provisions for handling or concentrating microbes, such as membranes, packing, settling and recycling.

The principle component of the biogas produced by the process is a renewable form of methane. The biogas is optionally treated to remove at least a portion of one or more impurities. Such impurities may include, without limitation, carbon dioxide and hydrogen sulfide. In an embodiment of the invention, at least carbon dioxide is removed from the biogas. The degree of removal of the one or more impurities may be at a level sufficient to meet pipeline specifications. For example, at least 70% of the carbon dioxide, at least 80% of the carbon dioxide, at least 90% of the carbon dioxide or at least 95% of the carbon dioxide may be removed by weight from crude biogas (wt:wt). Examples of techniques for impurity removal include known techniques such as water or solvent scrubbing, pressure swing absorption and/or membrane separation.

Recycle of One or More Process Streams

According to an embodiment, a liquid stream or a portion thereof originating from an anaerobic digester is introduced back to the digester or upstream in the process as part of a recycle. The liquid stream originating from the anaerobic digester, also referred to herein as an "effluent stream" may be obtained by conducting a solids-liquid separation from a stream exiting an anaerobic digester or without such solids-liquid separation. In a further embodiment, introduction of the liquid stream to the digester or upstream is conducted by recycling an internal stream within the digester itself.

Introduction of the liquid stream back to a digester or upstream in the process, such as to the solids-liquid separation may increase the amount of extractives that can be fed to a digester. Without such recycle, the aqueous stream comprising extractives may be too concentrated and toxic to the microorganisms, which can reduce the efficiency of the process. By recycling of the liquid stream, the concentration of toxic extractives is reduced, and thereby anaerobic digestion can be made operational without excess use of water for dilution. Recycle may also result in an effluent stream from a digester with a higher salt concentration than could otherwise be achieved, which can reduce the cost of subsequent processing to remove water, such as evaporation or reverse osmosis to dispose of such effluent streams. Recovery of salts from the liquid stream from the digester can also provide a stream that is less costly to dispose of or process and, in addition, the recovered salts can be used as a saleable product or can be re-used in the process to reduce chemical demand.

In one embodiment of the invention, introducing the liquid stream or a portion thereof originating from the digester back to the digester or upstream of the digester results in an increase in the concentration or purity of potassium in an effluent stream from the anaerobic digester. The potassium can be recovered from the effluent stream for use as a fertilizer or can be re-used in the process. For example, potassium salts can be recovered and used as a fertilizer. Re-use in the process may comprise introducing a potassium containing stream to a process stream to increase its pH thereof. Examples of such process streams include a stream comprising pretreated feedstock or a stream fed to a fermentation comprising sugar.

In a further embodiment, inorganic salt, including a potassium salt, can be recovered from a purge stream. In such embodiment, an inorganic salt-containing liquid stream introduced back to the digester or upstream in the process is purged, meaning that a portion of such liquid stream is withdrawn as explained above. Purging typically has the effect of reducing accumulation of soluble components which may otherwise build up during recycle. The purging of the liquid stream to produce the main stream and the purge stream can be conducted on a continuous or periodic basis. The main stream and the purge stream are distinguished by volume, with the volume of the purge stream being less than that of the main stream. The inorganic salt may then be recovered by known techniques and re-used in the process, used off-site or provided for use as a vendible product.

The purge stream may be subjected to a water removal step to produce a concentrated salt stream. As described, removing water from the purge stream is more energy efficient than water removal from the complete salt-containing stream withdrawn from the digester. Improvements in energy efficiency in turn can lead to GHG reductions as described herein (Example 1 and 2). The removed water can optionally be recycled in the process. A concentrated inorganic salt-containing stream from which the water has been removed can then be processed more readily. For example, the concentrated stream can be more easily disposed of or inorganic salt can be more readily recovered therefrom for use as fertilizer or the concentrated stream can be re-used in the process to at least partially neutralize acid, as described herein.

The foregoing water removal step may utilize evaporation, concentration with membranes, freeze crystallization and/or other water removal techniques known to those of skill in the art.

In a further embodiment of the invention, lime is added to the liquid stream to precipitate calcium carbonate and potassium hydroxide is recovered as a base for sale or use in the process.

In an embodiment of the invention, the aqueous stream comprising the one or more extractives fed to the anaerobic digester comprises at least sulfur. The sulfur may arise from the addition of a sulfur-containing process chemical such as sulfuric acid or sulfur dioxide to a stage upstream of the digester. The sulfur may be volatilized to hydrogen sulfide during the anaerobic digestion by sulfate or sulfite reducing bacteria. The resultant hydrogen sulfide may then be treated to produce elemental sulfur or oxides of sulfur, such as sulfur dioxide. An acid comprising sulfuric acid, sulfurous acid, sulfur dioxide or a combination thereof may be recovered from the elemental sulfur or oxides of sulfur. This acid may then be used in the process at a step requiring a sulfur catalyst. A non-limiting example of such a step is pretreatment or acid soaking, although the acid can be used to neutralize alkali as well in other steps of the process. Neutralization of the alkali may be partial or complete.

In a further embodiment of the invention, a condensate stream may be introduced to the anaerobic digester or upstream of the digester. The process condensate stream is obtained from a vapour stream that is condensed after a thermodynamic separation process. Thermodynamic separation processes include those that separate streams based upon differences in their boiling points and include, but are not limited to, flash cooling, distillation and evaporation.

In one embodiment of the invention, the process condensate stream is flash condensate, an evaporator condensate, an overhead stream or a combination thereof. The flash condensate may arise from pretreatment or other stages in which a process stream is subject to a pressure and temperature change, such as by flashing. Evaporator condensate may originate from evaporation of a still bottoms stream or a purge stream, described in more detail below. The condensate stream may also be an overhead stream from distillation or steam stripping.

The condensate stream can be introduced to the digester, or in a stage upstream of the digester, in combination with other streams. If more than one condensate stream is introduced to the digester, they may be combined and then fed to the anaerobic digester or fed separately.

The process condensate stream may comprise an organic acid such as acetic acid. Thus, the introduction of a process condensate in a stage upstream of anaerobic digestion or to the digester itself may increase the concentration of acetic acid, acetate, or a combination thereof, in the anaerobic digestion, which may increase the yield of biogas. Moreover, the process condensate stream will generally contain a lowered concentration of inorganic salts, such as potassium salts as these salts are not volatile. This is advantageous as the process condensate stream can be introduced to pretreatment, or upstream of such stage, without causing the buffering effects described previously that result when certain salts are present during addition of pretreatment chemical.

According to one particularly advantageous embodiment of the invention, a purge stream from a stream originating from the anaerobic digester is sent to evaporation. The evaporation of the purge stream produces a condensate stream that can be fed to various stages of the process, including pretreatment, as discussed above. On the other hand, the effluent stream, which is a salt-containing stream from an anaerobic digester, can be fed back to stages of the process downstream of pretreatment to avoid the above-described buffering effects. Using such a configuration in the process for recycle can improve process economics and reduce GHG emissions relative to other process configurations. Evaporating only a portion of the salt-containing stream exiting the anaerobic digester reduces the costs of evaporation and this in turn can reduce the GHG emissions associated with the process. A non-limiting example of such a process is described in FIG. 2.

While an effluent stream from the digester and a process condensate stream are described as suitable streams for recycle, streams from other stages may be recycled as well. Examples of other streams from the process that can optionally be fed to an anaerobic digester include spent cleaning solutions, rectifier effluent, blowdown streams, regenerated streams and/or spent seal water.

Biogas or Products Derived Therefrom

The biogas from which one or more impurities have been removed may be provided for use as a transportation or heating fuel. The biogas can be used directly as a fuel. For example, the biogas can be used as compressed natural gas or liquid natural gas to power vehicles or for heating. Furthermore, the biogas can be used to produce one or more products therefrom, which means a product or products produced directly or indirectly from biogas. Examples of such products are described further below.

When using biogas as a transportation or heating fuel, it may be introduced to an apparatus for transporting methane, such as a pipeline. Government authorities have recognized that it does not make any difference, in terms of the beneficial environmental attributes associated with the use of biogas, whether the displacement of fossil fuel occurs in a fungible natural gas pipeline, or in a specific fuel production facility that draws methane from that pipeline. Thus, according to this embodiment, methane withdrawn from the pipeline is considered renewably derived or to have the GHG emission attributes of the biogas introduced thereto. In other words, the withdrawn methane is considered to have the GHG emission value of the biogas introduced to the apparatus, even though the methane may not contain actual molecules from the original cellulosic feedstock from which it is derived. For such GHG emission attributes to be recognized, the amount of biogas introduced to the apparatus and the amount withdrawn typically should be the same. However, according to some embodiments, the invention is not constrained by the exact amounts of biogas introduced to the apparatus and the amounts withdrawn, and whether such amounts correspond precisely.

In a further embodiment of the invention, the biogas is transported by truck, rail or by shipping over a body of water. A combination of such modes of transportation can also be used.

As mentioned, one or more products derived from the biogas can also be used as a transportation or heating fuel. For example, a product derived from biogas may be produced by using the biogas as an intermediate or feedstock for producing another fuel or within a stage for producing another fuel, including upstream stages. According to such embodiment, biogas may be introduced to an apparatus for transporting methane. Another party may then withdraw an amount of methane from the apparatus as a feedstock for producing another fuel. As described above, the amount of methane withdrawn has the GHG emission attributes of the amount of biogas introduced to the apparatus.

The biogas or methane having the GHG emission reductions of the biogas removed from the apparatus can be used to make renewable hydrogen. Such renewable hydrogen includes hydrogen sourced from (i) biogas derived from anaerobic digestion; or (ii) methane, including natural gas or fossil fuel derived methane or hydrogen that is fossil fuel derived, which qualifies under applicable laws and regulations to be treated as renewably derived.

The renewable hydrogen can be produced by a variety of different processes. Examples of such processes include autothermal reforming ("ATR") and steam methane reforming ("SMR") and additionally water gas shift reactions or other like technologies as known to those skilled in the art. Both ATR and SMR methods operate by exposing the biogas or methane withdrawn from the apparatus to a catalyst at high temperature and pressure to produce syngas, which is renewable hydrogen and carbon monoxide. The carbon monoxide generated by either method may be generally further reacted with water in a water gas shift reaction to form carbon dioxide and renewable hydrogen. SMR converts the methane into renewable hydrogen and carbon monoxide without oxygen. The carbon monoxide reacts further to produce more renewable hydrogen in the water gas shift reaction. The relevant equations are as follows:

$$CH_4 + H_2O \rightarrow CO + 3H_2$$

$$CO + H_2O \rightarrow CO_2 + H_2$$

Without being limiting, conventional steam reforming plants may operate at pressures between 200 and 600 psi with outlet temperatures in the range of 815 to 925° C.

ATR uses oxygen and carbon dioxide or steam in a reaction with methane to form syngas and water. The reaction may take place in a single chamber where the methane is partially oxidized. The reaction is exothermic due to the oxidation. The reactions can be described in the following equations, using CO2:

$$2CH_4 + O_2 + CO_2 \rightarrow 3H_2 + 3CO + H_2O$$

and using steam:

$$4CH_4 + O_2 + 2H_2O \rightarrow 10H_2 + 4CO.$$

A difference between SMR and ATR is that SMR uses no oxygen.

SMR and ATR are carried out in any suitable device or devices for producing renewable hydrogen from a combustible fluid feedstock and include devices and operations that are known or used in the art for such purposes. The steam reforming operation may be situated in the fuel production facility or the operation may be a separate plant located off-site.

It is preferred that the renewable hydrogen produced by SMR or ATR be purified to remove one or more non-hydrogen components. The hydrogen may be purified by methods known to those skilled in the art, such as a liquid absorption system for carbon dioxide removal or a pressure swing absorption operation to produce a purified hydrogen product.

Although the production of renewable hydrogen from methane by SMR or ATR is described, renewable hydrogen can also be recovered from the syngas, $CO+3H_2$. Renewable hydrogen may be used directly as a transportation or heating fuel or converted into another fuel.

After production, the renewable hydrogen may be used in a process to produce a liquid transportation or heating fuel. For example, the renewable hydrogen may be combined with a crude oil derived liquid hydrocarbon so that it becomes incorporated into the hydrocarbon and ultimately becomes part of the liquid transportation or heating fuel that is the product of the fuel production facility. (See, for example, U.S. Pat. Nos. 8,753,843 and 8,658,026, which are incorporated herein by reference).

By the term "crude oil derived liquid hydrocarbon", it is meant any carbon-containing material derived from crude oil that is liquid at standard ambient temperature and pressure. Crude oil includes liquid, gaseous and solid carbon-containing material from geologic formations, including oil reservoirs, such as hydrocarbons found within rock formations, oil sands or oil shale. Advantageously, since the hydrogen that is added to the crude oil derived liquid hydrocarbon is renewable, the resultant transportation or heating fuel is considered a fuel having renewable content, or reduced fossil fuel content.

The incorporation of renewable hydrogen into the crude oil derived liquid hydrocarbon according to the present invention encompasses the addition, incorporation or bonding of renewable hydrogen to crude oil derived liquid hydrocarbon. Such reactions include hydrogenation, which includes, without limitation, any reaction in which renewable hydrogen is added to a crude oil derived liquid hydrocarbon through a chemical bond or linkage to a carbon atom. The renewable hydrogen may become bonded to a carbon backbone, a side chain, or a combination thereof, of a linear or ring compound of a crude oil derived liquid hydrocarbon. Hydrogenation reactions may be carried out in the presence of a catalyst. The addition or incorporation of renewable hydrogen into the crude oil derived liquid hydrocarbon can be achieved by the addition of the renewable hydrogen to an unsaturated or a saturated hydrocarbon. This includes addition of renewable hydrogen to unsaturated groups, such as alkenes or aromatic groups, on the crude oil derived liquid hydrocarbon. Furthermore, the addition or incorporation of hydrogen may be accompanied by the cleavage of a hydrocarbon molecule. This may include a reaction that involves the addition of a hydrogen atom to each of the molecular fragments that result from the cleavage. Without being limiting, such reactions may include ring opening reactions and/or dealkylation reactions. Other reactions that may involve the addition of hydrogen include reactions carried out prior to isomerization and cyclization. Such reactions are described in U.S. Pat. Nos. 8,753,843 and 8,658,026.

The hydrogenation reactions may be conducted in a "hydrogenation reactor". As used herein, the term "hydrogenation reactor" includes any reactor in which hydrogen is added to a crude oil derived liquid hydrocarbon. The hydrogenation reactor may be a hydrocracking reactor or a "hydrocracker" or any other reactor in which hydrogen becomes bonded to a crude oil derived liquid hydrocarbon, as described hereinafter.

Examples of processes in which hydrogenation reactions occur include hydrocracking and hydrotreating. Hydrocracking typically employs a catalyst and hydrogen. Hydrocracking reactions involve the conversion of relatively high-boiling, high molecular weight hydrocarbons into lower-boiling, lower molecular weight hydrocarbons by the breaking of carbon-to-carbon bonds. The breaking of carbon-to-carbon bonds also referred to herein as "cracking" or "hydrocracking", may be carried out in a hydrogenation reactor. In embodiments of the invention, the cracking in the presence of renewable hydrogen can be carried out in a hydrocracker.

Hydrotreating also typically employs a catalyst and hydrogen. The catalyst converts organic sulfur in crude oil derived hydrocarbons to $H_2S$. The $H_2S$ gas may be removed by known techniques. Additionally, the hydrotreating may convert organic nitrogen to ammonia and/or oxygen to water.

According to some embodiments, as would be appreciated by those of skill in the art, the reactor may use an amorphous catalyst that carries out both hydrotreating and hydrocracking. In yet a further embodiment, a crude oil derived liquid hydrocarbon is at least partially desulfurized and then fed to a hydrocracker.

Another example of products derived from biogas are products produced by a Fischer Tropsch reaction. This may involve providing the biogas, or methane having the GHG emission attributes of the biogas, to a process in which such biogas or methane is reacted to form syngas, which comprises carbon monoxide and hydrogen, in a steam reformation process. The syngas is subsequently converted into liquid hydrocarbons in a Fischer Tropsch process. A Fischer Tropsch process uses a catalyst to convert carbon monoxide to hydrocarbons, such as alkanes, although other reaction products may result as well.

Other products besides hydrocarbons may be produced from syngas. Such products include methane, hydrogen, ammonia, dimethyl ether, methanol, ethanol, liquid hydrocarbons, electricity and steam.

In one advantageous embodiment of the invention, syngas is used to produce ethanol. According to such embodiment, syngas can be reacted to produce methanol, which subsequently may be reacted with carbon monoxide to produce acetic acid or acetate. The acetic acid or acetate in turn can be reacted with hydrogen to produce the ethanol.

Providing the Solids Stream to a Thermal Process

A solids stream comprising the insoluble components is provided to a thermal process, which is any process that includes one or more stages in which heat is generated and/or inputted. The solids stream provided to the thermal process may comprise lignin, cellulose or a combination thereof.

The solids stream may be obtained from the solids-liquid separation described previously or may be any other stream derived therefrom arising from the process comprising insoluble components. For example, the solids stream from the solids-liquid separation may be further treated in one or more chemical, heat and/or biological treatment steps and a solids stream remaining after one or more of such treatments may be provided to the thermal process. Optionally, the solids stream comprising the insoluble components is from any stage of a conversion process to produce a fuel or chemical that includes pretreating a cellulosic feedstock to disrupt fiber structure and improve accessibility of cellulose to a subsequent enzymatic or chemical treatment, enzymatic or chemical hydrolysis to hydrolyze cellulose to glucose, fermentation of glucose to a product.

As described previously, the use of a solids stream from which at least a portion of the extractives has been removed has the advantage that less ash and/or other undesirable components are produced during the thermal process. Ash can be particularly problematic as it can form a low melting material produced by the combination of silica with alkali salts. This low melting point material can lead to fouling or slagging of boilers or gasification units, requiring shutdowns and expensive cleaning. Some components can also contribute to problematic tars in gasification operations. Advantageously, the removal of extractives prior to gasification can reduce the formation of such tars.

Another advantage of using the solids stream is that chloride can be reduced or eliminated. Chloride is corrosive to certain metals commonly used in thermal processing equipment and thus by reducing the concentration of this component the process equipment is less prone to corrosion or need not be constructed with corrosion resistant material.

In one embodiment of the invention, the solids stream obtained from the solids-liquid separation described previously has liquid removed therefrom in a second or subsequent solids-liquid separation to produce a concentrated solids stream. This can reduce the transport cost and typically increases the efficiency of the thermal process due to the reduced water content. The solids content of the stream resulting from the first solids-liquid separation is generally greater than 30 wt %, more typically greater than 50 wt % (w/w). Between about 30 wt % and about 95 wt % (w/w) of the water may be removed from the solids stream in the second or subsequent solids-liquid separation to produce the concentrated solids. The step of removing water from the solids stream may comprise a step of drying.

The solids may be densified or compressed to form densified solids, such as pellets. According to one embodiment of the invention, greater than 90% of the densified or compressed solids by weight are greater than ¼ inches in length or diameter. The size of the densified or compressed solids is measured by passing the solids through round openings of ¼ inch in diameter. In certain embodiments the solids are densified or compressed to form densified material of defined shapes, such as pellets, briquettes, cubes, pucks, cylinders or other shapes. The densification or compaction may be carried out by mechanical densification, torrefaction or other methodologies as known to those of skill in the art.

The liquid removed from the solids stream as a result of the first or any subsequent solids-liquid separation can be introduced back to the digester or upstream of the digester. The liquid in this typically aqueous stream may comprise extractives that are inhibitory to yeast or enzymes used in the process. However, the extractives may not be inhibitory to the microorganisms in the anaerobic digestion. Further, introducing this stream can also dilute the feed stream to the anaerobic digestion which in turn reduces the concentration of components that may be toxic to the microbes.

The thermal process encompasses processes that include combustion, gasification, pyrolysis or a combination thereof. Combustion includes one or more exothermic reactions between a fuel and an oxidant producing heat. As described below, combustion may be used to generate heat or produce power.

Gasification of the solids may include heating at elevated temperature to produce syngas, which includes carbon monoxide and hydrogen. The syngas can in turn be used as an intermediate to produce another fuel (such as methane) as described below. In another embodiment, the hydrogen produced by gasification of the solids is used in a hydrogenation process carried out to produce another fuel, such as a hydrocarbon fuel as described above. Gasification is typically carried out in the presence of oxygen. Pyrolysis includes heating at elevated temperature to produce syngas, char and/or pyrolysis oil and may be carried out in the absence of oxygen or at low levels thereof. The thermal process can be carried out in the presence of a catalyst or without a catalyst.

Products Produced or Derived from the Thermal Process

According to an aspect of the invention, one or more products produced or derived from the thermal process displace a product made from fossil fuel. Products produced by the thermal process are also referred to herein as "energy products". By energy product, it is meant a product that stores chemical, heat or electrical energy and encompasses fuels, fuel intermediates, steam and electricity. By "one or more products derived therefrom", it is meant products produced directly or indirectly from an energy product produced by thermal processing. Examples of such products are described below.

By "displace", with reference to an energy product, it is meant that the energy product produced by the thermal process, or an energy product derived therefrom, displaces a corresponding energy product produced from fossil fuel energy sources. The GHG emissions to produce the energy product are thereby reduced because the GHG emissions associated with the displaced energy product from fossil fuel are avoided, and replaced with an energy product produced or derived from cellulosic feedstock. The energy product produced from fossil fuel energy sources may be referred to as a fossil derived product.

Examples of fuel or fuel intermediate products produced or derived from the thermal process include syngas, hydrogen, methane and pyrolysis oil. Syngas, hydrogen, methane and pyrolysis oil can be used as transportation or heating fuel or as an intermediate to make such fuels.

Syngas, which comprises hydrogen, carbon monoxide and optionally other gaseous components can be used as a fuel itself or more typically to produce another fuel. Syngas is produced by gasification and/or pyrolysis of cellulosic feedstock. Examples of products made from syngas include methane, hydrogen, ammonia, dimethyl ether, methanol, ethanol, liquid hydrocarbons, electricity and steam.

In an embodiment of the invention, methane is produced from syngas. The production of methane from syngas includes a methanation reaction, which is typically conducted over metal catalysts at elevated temperature and pressure. The chemical reaction for producing methane from syngas is as follows:

$$CO + 3H_2 \rightarrow CH_4 + H_2O$$

The methane produced from the above reaction can be introduced to an apparatus for transporting methane. An amount of methane withdrawn from the apparatus has the GHG emission attributes of the amount of methane produced from the syngas introduced to the apparatus, as discussed previously in connection with biogas. This amount of methane withdrawn is considered renewable. The withdrawn methane can be used to make renewable hydrogen and the renewable hydrogen can be used to hydrogenate a crude oil derived liquid hydrocarbon as described previously.

The syngas can also be used to make liquid hydrocarbons by a Fischer Tropsch process as described previously.

In one advantageous embodiment of the invention, syngas is used to produce ethanol. As described previously, syngas can be reacted to produce methanol, which subsequently may be reacted with carbon monoxide to produce acetic acid and/or acetate. The acetic acid or acetate in turn can be reacted with hydrogen to produce ethanol.

Methanol produced from syngas can also be used to make gasoline. The methanol can be dehydrated to dimethylether. Subsequently, an equilibrium mixture of methanol, dimethylether and water is converted to short chain olefins. In a further reaction step, the short-chain olefins are reacted to form higher olefins, including n/iso-paraffins, aromatics and naphthenes.

Alternatively, hydrogen from the syngas can be used to hydrogenate a crude oil derived liquid hydrocarbon, as described previously in connection with biogas. According to such an embodiment, hydrogen is recovered from syngas and/or produced in a further water gas shift reaction. The hydrogen may be produced on-site at a fuel production facility where crude oil or crude oil derived hydrocarbons are processed or at an off-site location. The renewable hydrogen can subsequently be used to hydrogenate a crude oil derived liquid hydrocarbon as described previously. Hydrogen can also be transported via an apparatus such as a pipeline, similar to transporting methane. According to such embodiment, hydrogen withdrawn from the apparatus will have the GHG emission attributes of an amount introduced that is produced from the syngas, even though the hydrogen may not contain actual molecules from the original cellulosic feedstock from which the hydrogen is derived. Hydrogen from syngas or hydrogen from fossil fuel sources having the GHG emission attributes of hydrogen from syngas is referred to as renewable hydrogen.

Another product that may be produced by the thermal process is pyrolysis oil. Pyrolysis oil, also referred to as bio-oil, is produced by subjecting the solids stream to pyrolysis at elevated temperature, typically lower than gasification. Pyrolysis may degrade the feedstock to produce pyrolysis oil, syngas and/or char. Pyrolysis oil can be treated further to produce a transportation fuel such as diesel or used directly as a fuel.

Steam and electricity may be produced in the thermal process by combustion of the solids stream or indirectly by combusting a fuel product produced by the thermal process. The heat generated from the combustion may be utilized to produce products such as steam, process heat, building heat, electricity, or any combination of these products. The steam or electricity can be used in any production process to produce a fuel or chemical or in a power generating facility (e.g. a facility to generate power to supply the power grid).

As mentioned, the foregoing energy products may be used to displace a product made from fossil fuel or fossil derived product. For example, the syngas produced by the invention may displace syngas made from natural gas, oil or coal. The hydrogen produced by the present invention may displace hydrogen produced from fossil natural gas. The biogas, or methane from the thermal process, displaces natural gas that is obtained from underground deposits or from gasification of fossil fuel such as coal, also referred to as synthetic natural gas. Pyrolysis oil may displace diesel oil from fossil sources.

Such displacement contributes at least in part to reductions in life cycle GHG emissions and can allow for advantaged fuel credit generation, as discussed below.

Quantifying GHG Emission Reductions

In certain embodiments, the process of the invention involves providing one or more products obtained or derived from anaerobic digestion, the thermal process, or both processes, for use as a transportation or heating fuel which has reduced life cycle GHG emissions. Providing includes supplying or directly or indirectly causing one or more parties to supply one or more of such products for use as a transportation or heating fuel. The one or more products obtained or derived from the thermal process may include renewable hydrogen, a fuel or fuel intermediate formed by a reaction with syngas, or pyrolysis oil. The one or more products obtained or derived from anaerobic digestion include biogas, methane having the GHG emission attributes of the biogas, renewable hydrogen or a liquid hydrocarbon having renewable content.

By conducting the process steps as disclosed herein, the product for use as a transportation or heating fuel may have life cycle GHG emissions associated therewith that are at least 20%, 30% or 40% lower than a gasoline baseline. However, in certain embodiments, these savings can be at least as much as 50% lower than a gasoline baseline, or at least as much as 60%, 70%, 80%, 90% or 100% lower than a gasoline baseline.

To determine life cycle GHG emissions associated with a product for use as transportation or heating fuel, analyses are conducted to calculate the GHG emissions related to the production and use of the fuel throughout its life cycle. Life cycle GHG emissions include the aggregate quantity of GHG emissions related to the full life cycle of the transportation or heating fuel, including all stages of fuel and feedstock production and distribution, from feedstock generation or extraction through the distribution and delivery and use of the finished fuel to the ultimate consumer. GHG emissions account for total net GHG emissions, both direct and indirect, associated with feedstock production and distribution, the fuel production and distribution and use.

Because many of the laws adopted differentiate the requirements for fuels based upon their net GHG emissions impacts, it is known to those skilled in the art that regulators have developed and/or adopted methods to analyze and characterize the expected net GHG emissions of fuel pathways. Thus, the life cycle GHG emissions are determined in accordance with prevailing rules and regulations.

Life cycle GHG emissions evaluations generally consider GHG emissions associated with each of:

(a) feedstock production and recovery, including the source of carbon in the feedstock, direct impacts such as chemical inputs, energy inputs, and emissions from the collection and recovery operations, and indirect impacts such as the impact of land use changes from incremental feedstock production;

(b) feedstock transport, including feedstock production and recovery and GHG emissions from feedstock transport including energy inputs and emissions from transport;

(c) fuel production, including chemical and energy inputs, emissions and byproducts from fuel production (including direct and indirect impacts); and (d) transport and storage of the fuel prior to use as a transportation or heating fuel, including chemical and energy inputs and emissions from transport and storage.

Examples of models to measure life cycle GHG emissions associated with the one or more products of the invention, include, but are not limited to:

(i) GREET Model—GHGs, Regulated Emissions, and Energy Use in Transportation, the spread-sheet analysis tool developed by Argonne National Laboratories;

(ii) FASOM Model—a partial equilibrium economic model of the U.S. forest and agricultural sectors developed by Texas A&M University;

(iii) FAPRI International Model—a worldwide agricultural sector economic model that was run by the Center for Agricultural and Rural Development ("CARD") at Iowa State University;

(iv) GTAP Model—the Global Trade Analysis Project model, a multi-region, multi-sector computable general equilibrium model that estimates changes in world agricultural production as well as multiple additional models; and (v) ISO (International Organization for Standardization) standards for GHG emissions accounting and verification—provides guidance for quantification, monitoring and reporting of activities intended to cause greenhouse gas (GHG) emission reductions or removal enhancements.

The life cycle GHG emissions or carbon intensity of the products of the invention are measured in carbon dioxide equivalents ($CO_2$eq). As would be understood by those of skill in the art, carbon dioxide equivalents are used to compare the emissions from various GHGs based upon their global warming potential (GWP), which is a conversion factor that varies depending on the gas. The carbon dioxide equivalent for a gas is derived by multiplying the amount of the gas by the associated GWP.

grams of $CO_2eq$=((grams of a gas)*(GWP of the gas))

The GWP conversion value used to determine g $CO_2eq$ will depend on applicable regulations for calculating life cycle GHG emissions reductions. The GWP under EISA is 1, 21 and 310, respectively, for carbon dioxide, methane and nitrous oxide as set forth in Renewable Fuel Standard Program (RFS2) Regulatory Impact Analysis, February 2010, United States Environmental Protection Agency, EPA-420-R-10-006, pg. 13, of which the entire contents are incorporated herein by reference. Under California's LCFS, the GWP is 1, 25 and 298, respectively, for carbon dioxide, methane and nitrous oxide, as measured by the GREET model. It should be appreciated that GWP values can be readily calculated by those of skill in the art in accordance with regulations.

The unit of measure for carbon intensity or life cycle GHG emissions that may be used to quantify GHG emissions of the product of the present invention is grams $CO_2eq$ per MJ of energy in the fuel or grams $CO_2eq$ per million British thermal units of energy in the fuel (MMBTU). The units used to measure life cycle GHG emissions will generally depend on applicable regulations. For example, under the EPA regulations, GHG emissions are measured in units of grams $CO_2eq$ per million BTUs (MMBTU) of energy in the fuel. Under LCFS, GHG emissions are measured in units of grams $CO_2eq$ per MJ of energy in the fuel and are referred to as carbon intensity or CI.

The life cycle GHG emissions of the product of the invention are compared to the life cycle GHG emissions for gasoline, referred to as a gasoline baseline. GHG life cycle emissions are compared by reference to the use of gasoline per unit of fuel energy.

The EPA value for the gasoline baseline used in the life cycle GHG emission calculations is 98,204 g $CO_2eq$/MMBTU or 93.10 g $CO_2eq$/MJ. Under California's LCFS, the gasoline baseline is 95.86 g $CO_2eq$/MJ. Those of ordinary skill in the art can readily convert values herein from g $CO_2eq$/MJ to g $CO_2eq$/MMBTU or g $CO_2eq$/MMBTU to g $CO_2eq$/MJ by using an appropriate conversion factor.

According to certain embodiments of the invention, the life cycle GHG emission reduction relative to a gasoline baseline is measured "using EPA methodology", which means measuring life cycle GHG emissions reductions as disclosed in EPA-420-R-10-006, "Renewable Fuel Standard Program (RFS2) Regulatory Impact Analysis", February 2010, which is incorporated herein by reference.

According to a further embodiment of the invention, the life cycle GHG emission reduction relative to a gasoline baseline is measured using "LCFS methodology", which means measuring life cycle GHG emissions reductions by California's LCFS methodology using the GREET model, as set forth in Detailed California-Modified GREET Pathway for Corn Ethanol, California Environmental Protection Agency, Air Resources Board, Jan. 20, 2009, Version 2.0 which are incorporated herein by reference.

According to one embodiment of the invention, the life cycle carbon dioxide emissions, rather than the life cycle GHG emissions, are determined for the one or more products of the invention for use as a transportation or heating fuel and compared to a gasoline baseline.

Meeting Renewable and Low Carbon Fuel Targets

Embodiments of the invention advantageously provide a methodology for meeting renewable fuel targets or mandates established by governments, including legislation and regulations for transportation or heating fuel sold or introduced into commerce in the United States. Examples of such legislation include the Energy Independence and Security Act ("EISA") and California AB 32—The Global Warming Solutions Act, which respectively established an RFS and a Low Carbon Fuel Standard (LCFS). For example, under EISA, the mandated annual targets of renewable content in fuel are implemented through an RFS that uses tradable credits (called Renewable Identification Numbers, referred to herein as "RINs") to track and manage the production, distribution and use of renewable fuels for transportation or other purposes. Targets under the LCFS can be met by trading of credits generated from the use of fuels with a lower GHG emission value than the gasoline baseline.

The term "credit", "renewable fuel credit" or "fuel credit" means any rights, credits, revenues, offsets, greenhouse gas rights or similar rights related to carbon credits, rights to any greenhouse gas emission reductions, carbon-related credits or equivalent arising from emission reduction trading or any quantifiable benefits (including recognition, award or allocation of credits, allowances, permits or other tangible rights), whether created from or through a governmental authority, a private contract or otherwise. According to one embodiment of the invention, the renewable fuel credit is a certificate, record, serial number or guarantee, in any form, including electronic, which evidences production of a quantity of fuel meeting certain life cycle GHG emission reductions relative to a baseline set by a government authority. Preferably, the baseline is a gasoline baseline. Non-limiting examples of credits include RINs and LCFS credits.

The fuel credit may be generated as a result of one or more of the products from anaerobic digestion, the thermal process, or a combination thereof, or products derived therefrom that are used as a transportation or heating fuel. In further embodiments of the invention, the fuel credit relates to one or more of such products.

For example, the product of the invention could qualify for an advanced biofuel RIN under EISA having a D code of 3, 4, 5 or 7. In a further embodiment, the product of the invention is eligible for a RIN having a D code of 3 or 5. Under the LCFS, products for use as fuels with greater reductions in life cycle GHG emissions qualify for a greater number of credits having higher market value than fuels with lower reductions.

The presence of acetic acid and/or acetate in anaerobic digestion can also result in a greater yield of fuel than could otherwise be attained. For example, the product yield from cellulosic biomass in a process to produce a fuel can potentially be increased by at least 2% or by at least 3% relative to the same process where acetic acid and/or acetate is not introduced to anaerobic digestion to produce biogas. By increasing the yield from anaerobic digestion, a greater number of fuel credits can be generated from the cellulosic feedstock. Thus, the present invention also provides a process in which a greater yield of fuel credits are achieved relative to an otherwise identical process in which an aqueous stream comprising one or more extractives is not fed to anaerobic digestion.

According to an embodiment of the invention, a fuel credit is generated or caused to be generated with respect to the use of biogas as a transportation or heating fuel. According to such embodiment, a cellulosic feedstock is treated in one or more processing steps that release extractives therefrom. A solids-liquid separation is conducted on a process stream comprising the extractives and solids comprising insoluble components, thereby producing an aqueous stream comprising the extractives and a solids stream comprising insoluble components. An aqueous stream comprising one or more of the extractives or a portion of said aqueous stream is fed to an anaerobic digester to produce crude biogas. The process optionally involves removing at least a portion of one or more impurities from the crude biogas. Biogas is provided from anaerobic digestion, or one or more products derived from biogas, for use as a transportation or heating fuel. A renewable fuel credit is generated or caused to be generated. In certain embodiments of the invention, the aqueous stream comprises acetic acid, acetate or a combination thereof. Alternatively, or in addition, the foregoing process comprises obtaining a liquid stream from the anaerobic digester and introducing the liquid stream or a portion thereof to the digester or to a stage upstream of the digester.

The fuel credit may be generated by a producer or user of biogas, a party that carries out the thermal process or a party that uses a product produced by the thermal process. According to certain embodiments of the invention, the renewable fuel credit is caused to be generated by another party. According to such embodiments, a producer of biogas, a party that carries out the thermal process or a party processing the biogas or a product of the thermal process may cause an intermediary or other party, including a fuel blender or importer, to generate a credit.

The term "cause" or "causing", as used in the specification means to arrange or bring about, either directly or indirectly, or to play a role in a series of activities through commercial arrangements such as a written agreement, verbal agreement or contract.

Energy policy, including EISA and LCFS, and the generation of renewable fuel credits under each of these legislative frameworks, is discussed in turn below.

(i) Meeting Renewable Fuel Targets Under EISA

U.S. policymakers have introduced a combination of policies to support the production and consumption of biofuels, one of which includes the RFS. The RFS originated with the Energy Policy Act of 2005 (known as RFS1) and was expanded and extended by the EISA of 2007. The RFS expanded and extended under EISA is sometimes referred to as RFS2 or RFS as used herein.

Under the EISA, the RFS sets annual mandates for renewable fuels sold or introduced into commerce in the United States through 2022 for different categories of biofuels (see Table 2 below). There is an annually increasing schedule for minimum aggregate use of total renewable biofuel (comprised of conventional biofuels and advanced biofuels), total advanced biofuel (comprised of cellulosic biofuels, biomass-based diesel, and other advanced biofuels), cellulosic biofuel and bio-based diesel. The RFS mandates are prorated down to "obligated parties", including individual gasoline and diesel producers and/or importers, based on their annual production and/or imports.

Each year, obligated parties are required to meet their prorated share of the RFS mandates by accumulating credits known as RINs, either through blending designated quantities of different categories of biofuels, or by purchasing from others the RINs of the required biofuel categories.

The RIN system was created by the EPA to facilitate compliance with the RFS. Credits called RINs are used as a currency for credit trading and compliance. RINs are generated by producers and importers of renewable biofuels and assigned to the volumes of renewable fuels transferred into the fuel pool. RINs are transferred with a fuel through the distribution system until they are separated from the fuel by parties who are entitled to make such separation (generally refiners, importers, or parties that blend renewable fuels into finished fuels). After separation, RINs may be used for RFS compliance, held for future compliance, or traded. There is a centralized trading system administered by the U.S. EPA to manage the recording and transfer of all RINs.

According to certain embodiments of the invention, a RIN may be characterized as numerical information. The RIN numbering system was in the format KYYYYCCCCFFFFFBBBBBRRDSSSSSSSSEEEEEEEE where numbers are used to designate a code representing whether the RIN is separated from or attached to a specific volume (K), the calendar year of production or import (YYYY), Company ID (CCCC), Facility ID (FFFFF), Batch Number (BBBBB), a code for fuel equivalence value of the fuel (RR), a code for the renewable fuel category (D), the start of the RIN block (SSSSSSSS) and the end of the RIN block (EEEEEEEE) Under current regulations, a RIN contains much of the foregoing information and other information in the form of data elements that are introduced into a web-based system administered by the EPA known as the EPA Moderated Transaction System, or "EMTS". It should be appreciated, however, that the information required for RIN generation and/or the format of the information may change depending on prevailing regulations.

The D code of a RIN specifies the fuel type, feedstock and production process requirements and thus in certain embodiments of the invention the D code may be used to characterize the type of RIN, as described hereinafter. The D code of a RIN is assigned a value between 3 and 7 under current regulations. The value assigned depends on the fuel type, feedstock and production process requirements as described in Table 1 to 40 C.F.R. § 80.1426. Examples of fuels assigned a D code of 3-7 under current regulations are provided below. These examples are for illustration purposes only and are not to be considered limiting to the invention.

TABLE 1

RIN D code examples

| D code | Fuel Type | Example |
| --- | --- | --- |
| 3 | Cellulosic biofuel | Ethanol from cellulosic biomass from agricultural residues |
| 4 | Biomass-based diesel | Biodiesel and renewable diesel from soy bean oil |
| 5 | Advanced biofuel | Ethanol from sugarcane |
| 6 | Renewable fuel (conventional biofuel) | Ethanol from corn starch |
| 7 | Cellulosic diesel | Diesel from cellulosic biomass from agricultural residues |

As described previously, the RFS2 mandate volumes are set by four separate but nested category groups, namely renewable biofuel, advanced biofuel, cellulosic biofuel and biomass-based diesel. The requirements for each of the nested category groups are provided in Table 2.

The nested category groups are differentiated by the D code of a RIN. To qualify as a total advanced biofuel, the D code assigned to the fuel is 3, 4, 5 or 7, while to qualify as cellulosic biofuel the D code assigned to the fuel is 3 or 7 (Table 2).

According to current regulations, each of the four nested category groups requires a performance threshold in terms of GHG reduction for the fuel type. In order to qualify as a renewable biofuel, a fuel is required to meet a 20% life cycle GHG emission reduction (or be exempt from this requirement), while advanced biofuel and biomass-based diesel are required to meet a 50% life cycle GHG emission reduction and cellulosic biofuels are required meet a 60% life cycle GHG emission reduction, relative to a gasoline baseline. As well, each nested category group is subject to meeting certain feedstock criteria.

TABLE 2

Nested category groups under RFS2

| Nested category group | Fuel type | Life cycle GHG threshold reduction relative to gasoline baseline |
|---|---|---|
| Renewable biofuel | Conventional biofuels (D code 6) and advanced biofuels (D code 3, 4, 5 or 7) | 20% |
| Advanced biofuel | Cellulosic biofuels (D code 3 or 7), biomass-based diesel (D code 4 or 7), and other advanced biofuels (D code 5) | 50% |
| Cellulosic biofuels | Biofuel derived from cellulosic material (D code 3) and bio-diesel derived cellulosic material (D code 7). | 60% |
| Biomass-based diesel | Conventional biodiesel (D code 4) or cellulosic diesel (D code 7) | 50% |

Thus, according to certain embodiments of the invention, a RIN credit containing information or a value corresponding to a reduction in life cycle GHG emissions relative to a baseline is generated with the production of a volume of one or more products produced by the process. The information may correspond to a reduction in life cycle GHG emissions of at least 40, 45, 50, 55, 60, 65, 70, 75, 80 or 85% relative to a gasoline baseline. The invention may contribute wholly or in part to achieving reductions in the life cycle GHG emissions of a product for use as a fuel relative to a gasoline baseline.

The RIN associated with one or more products obtained or derived from the process may be assigned a D code of 3, 4, 5 or 7, also referred to herein as a D3, D4, D5 and D7 RIN, respectively. According to certain embodiments, the RIN associated with the one or more products may be assigned a D code of 3 or 5. Under current regulations, this corresponds to cellulosic biofuel and advanced biofuel fuel types, which meet GHG emissions reductions of 60% and 50%, respectively, relative to a gasoline baseline.

According to some embodiments of the invention, the fuel credit is characterized as containing numerical information associated with the one or more products produced by the process of the invention for use as a transportation or heating fuel. Thus, a party may generate a fuel credit comprising numerical information relating to one or more products of the process representing at least one parameter selected from (i) the type of transportation or heating fuel; (ii) the year in which the product was produced; (iii) a registration number associated with the producer or importer; and (iv) serial number associated with a batch. In a further embodiment, at least two parameters or at least three parameters are selected from the foregoing list. These parameters relate to RIN generation, but a Low Carbon Fuel Standard (LCFS) credit may also require generation of numerical information pertaining to one or more of these parameters. The numerical information may also include one or more of the following parameters selected from: (i') a number identifying that the numerical information is assigned to a volume of the product, or separated; (ii') a registration number associated with the facility at which the product was produced or imported; (iii') a number representing a value related to an equivalence value of the product; (iv') a number representing a first-volume numerical information associated with a batch of the product; and (v') a number representing a last-volume numerical information associated with a batch of the product.

The RIN or numerical information described herein or portion thereof is provided to a government regulatory agency, including the EPA, in connection with generating a RIN. In some embodiments of the invention, the numerical information is also provided to a purchaser of the product produced by the invention. The numerical information described herein or portions thereof may be stored electronically in computer readable format.

The purchaser of the product for use as a transportation or heating fuel may separate the RIN. As described above, separation of a RIN from a volume of the product for use as a transportation or heating fuel, means termination of the assignment of the RIN to a volume of fuel. RIN separation is typically carried out by a fuel blender, importer or other obligated party. According to pre-2010 regulations, when a RIN is separated, the K code of the RIN is changed to 2.

Separation of RINs may be conducted in accordance with prevailing rules and regulations, as currently provided in 40 C.F.R. § 80.1129 and 40 C.F.R. § 80.1429. RINs generated in accordance with the invention may be separated and subsequently traded.

It should be understood that the regulations under EISA, including RIN requirements and the criteria for categorization of a fuel under a particular fuel category, such as life cycle GHG emission thresholds, are described herein in accordance with current regulations.

(ii) Low Carbon Fuel Standard (LCFS)

The beneficial GHG emissions reductions achieved by the present invention can provide a means for meeting low carbon fuel standards established by jurisdictions within the United States or other government authorities. The credit, which includes a certificate, may be associated with one or more products from the process, and represents or is proportional to the amount of life cycle GHG emissions reduced measured relative to a gasoline baseline. As set forth previously, the life cycle GHG emissions under low carbon fuel standards are often referred to as carbon intensity or CI.

California's LCFS currently requires that all mixes of fuel that oil refineries and distributors sell in the Californian market meet in aggregate the established targets for GHG emissions reductions. California's LCFS requires increasing annual reductions in the average life cycle emissions of most transportation fuels, up to a reduction of at least 10% in the carbon intensity, which is a measure of the life cycle GHG emissions, by 2020. Targets can be met by trading of credits generated from the use of fuels with a lower GHG emission value than gasoline baseline. Similar legislation has been implemented by the province of British Columbia, Canada, the United Kingdom and by the European Union.

According to some embodiments of the invention, LCFS fuel credit generation comprises generating information associated with the one or more products produced by the process of the invention for use as a transportation or heating fuel. A party may generate information relating to at least one parameter selected from (i) a reporting period; (ii) a fuel pathway code; (iii) transaction information, including type or date of a transaction; (iv) fuel production facility information; (v) fuel delivery methods; (vi) an amount of fuel used as a fossil fuel replacement, such as gasoline or diesel; and (vii) credits or deficits generated. In a further embodiment, information regarding at least two parameters, at least three parameters or at least four parameters is generated from the foregoing list.

British Columbia approved a Renewable and Low Carbon Fuel Requirements Act, which requires parties who manufacture or import the fuel into the province ensure that the renewable content and the average carbon intensity of the fuel they supply meets levels set by regulations. Fuel suppliers are required to submit annual reports regarding the renewable fuel content and carbon intensity of the transportation fuels they supply. The province allows transfers of GHG credits between fuel suppliers to provide flexibility in meeting the requirements of the regulation.

In the European Union, GHG emissions are regulated by a Fuel Quality Directive, 98/70/EC. In April 2009, Directive 2009/30/EC was adopted which revises the Fuel Quality Directive 98/70/EC. The revisions include a new element of legislation under Article 7a that requires fuel suppliers to reduce the GHG intensity of energy supplied for road transport (Low Carbon Fuel Standard). In particular, Article 7a specifies that this reduction should amount to at least 6% by 31 Dec. 2020, compared to the EU-average level of life cycle GHG emissions per unit of energy from fossil fuels in 2010. According to the Fuel Quality Directive, fuel/energy suppliers designated by member states of the European Union are required to report to designated authorities on: (a) the total volume of each type of fuel/energy supplied, indicating where the fuel/energy was purchased and its origin; and (b) the life cycle GHG emissions per unit of energy. The European Union has also promoted the use of biofuels through a Biofuel Directive (2003/30/EC), which mandates countries across the EU to displace certain percentages of transportation fuel with biofuels by target dates.

The United Kingdom has a Renewable Transport Fuel Obligation in which biofuel suppliers are required to report on the level of carbon savings and sustainability of the biofuels they supplied in order to receive Renewable Transport Fuel Certificates (RTFCs). Suppliers report on both the net GHG savings and the sustainability of the biofuels they supply according to the appropriate sustainability standards of the feedstocks from which they are produced and any potential indirect impacts of biofuel production, such as indirect land-use change or changes to food and other commodity prices that are beyond the control of individual suppliers. Suppliers that do not submit a report will not be eligible for RTFCs.

Certificates can be claimed when renewable fuels are supplied and fuel duty is paid on them. At the end of the obligation period, these certificates may be redeemed to the RTFO Administrator to demonstrate compliance. Certificates can be traded, therefore, if obligated suppliers do not have enough certificates at the end of an obligation period they have to 'buy-out' the balance of their obligation by paying a buy-out price.

The present invention has been described with regard to one or more embodiments. However, it will be apparent to persons skilled in the art that a number of variations and modifications can be made without departing from the scope of the invention as defined in the claims.

Examples

In the examples that follow, a cellulosic feedstock is treated to release extractives, which includes components such as inorganic salt, organic acids or salts of organic acids. This step is carried out as part of a pretreatment with acid or alkali to make the feedstock more amenable to subsequent hydrolysis with cellulase enzymes. After pretreatment, sugars are produced by addition of cellulase enzymes to the pretreated feedstock and the resultant sugars are fermented to ethanol, which is then recovered by distillation. Subsequently, a solids-liquid separation (SLS) is conducted on a process stream comprising the released extractives and solids containing insoluble components originating from the feedstock. In this example, the SLS is carried out on a process stream downstream of the ethanol production and recovery step, referred to as a still bottoms stream, although SLS can also be carried out upstream, such as on the pretreated feedstock. An aqueous stream resulting from the SLS is fed to an anaerobic digester to produce crude biogas, which is then purified and introduced to a pipeline and a corresponding amount of methane is withdrawn therefrom for ultimate use as a transportation fuel. The solids, in turn, are fed to a thermal process to produce an energy product, such as a chemical, heat or electrical energy.

As discussed previously, embodiments of the invention include recycle of an inorganic salt-containing liquid stream from the anaerobic digester to a stage downstream of pretreatment or to the anaerobic digester itself. By introducing the liquid stream from the digester downstream of pretreatment, the buffering effect of the salts present in this stream is avoided. This is advantageous as such salts can increase the chemical usage during pretreatment by resisting changes to the pH upon addition of pretreatment chemical, such as acid or alkali.

According to embodiments of the invention, the inorganic salt-containing stream is purged, which involves removing a portion of the salt-containing stream, to produce a purge stream. Such purge stream is evaporated and a condensate stream obtained from the evaporation is recycled in the process, although other water removal steps besides evaporation can be employed. This condensate stream does not contain high levels of salts, due to their low volatility, and thus can be recycled to pretreatment or upstream of this step without increasing pretreatment chemical usage, as would otherwise occur if such salts were introduced to pretreatment.

Therefore, recycling such a liquid stream from the digester containing inorganic salt and a condensate stream resulting from evaporation to separate stages of the process can enable the process to operate more efficiently relative to processes that do not implement such steps. Moreover, recycling in this manner leads to a process with more favourable life cycle GHG emissions relative to a gasoline baseline, as detailed below.

In order to illustrate the above-described advantages of the process, a comparative process is first described in Example 1, with reference to FIG. 1, and then in Example 2 the inventive process is described with reference to FIG. 2. Like reference numbers among the figures represent identical or similar streams or unit operations. Example 3 shows the favourable life cycle GHG emissions associated with the process of the invention relative to the comparative process.

Example 1: Description of a Comparative Process

As noted, in the comparative process illustrated schematically in FIG. 1, evaporation is conducted on the complete salt-containing liquid stream from the digester rather than a portion of the stream. Condensate from steam condensed in the evaporator is then recycled to the various stages of the process. As illustrated below, evaporating the whole salt-containing stream, rather than a portion thereof, and recycling only condensate is energy intensive and increases the GHG emissions of the process.

As shown in the comparative process of FIG. 1, a cellulosic feedstock slurry, in this case switch grass, is subjected to an extractive releasing step, in this case a pretreatment 2 which involves, for example, the addition of pretreatment chemical, such as acid, and heat to hydrolyze at least a portion of the xylan component of the cellulosic feedstock to release xylose and organic acids. The resultant pretreated cellulosic feedstock slurry 4 is then fed to ethanol production and recovery step 6.

In the ethanol production and recovery step 6, the cellulose component of the pretreated cellulosic feedstock slurry is hydrolyzed with cellulase enzymes to produce a hydrolyzed stream comprising glucose. The hydrolyzed stream, comprising glucose and other hexose and pentose sugars, as well as unhydrolyzed, insoluble material comprising lignin, is fed to yeast fermentation to produce a fermented solution containing ethanol. The fermented solution is sent to distillation which produces concentrated ethanol 7 and a remaining still bottoms stream 8.

The still bottoms stream 8 is sent to a SLS step 10 to produce a solids stream 12 and an aqueous liquid stream 14. The liquid stream 14 is sent to an anaerobic digestion unit 16. The anaerobic digestion unit 16 converts the organic components of the aqueous stream 16 to biogas to produce the biogas stream 18.

Both the biogas stream 18 and the solid stream 12 from the SLS 10 are fed to a combined heat and power generation (CHP) unit 20 (e.g. a boiler) where the solids and biogas are burned to generate heat and electricity for use within the process. This results in a GHG emissions saving because energy from fossil fuel need not be used to generate heat and electricity for plant operations. However, other stages of the process increase emissions, as detailed below in Example 3.

A stream 17 is withdrawn from the anaerobic digester 16 and subjected to a second SLS 22 to produce a salt-containing stream 24.

The salt-containing stream 24 is fed to an evaporation unit 26 to produce a condensate stream 30 and a concentrated salt stream 31. The condensate stream 30 is recycled by feeding to pretreatment 2, along with the incoming cellulosic feedstock slurry.

Example 2: Description of an Embodiment Employing Water Recycle

As noted above, embodiments of the invention involve purifying biogas from anaerobic digestion and introducing it to a pipeline from which methane is withdrawn for use as a transportation fuel. The GHG emissions associated with purifying the biogas from anaerobic digestion and introducing it to a pipeline result in a reduction to the life cycle GHG emissions per unit of fuel produced. This is off-set by the reductions in GHG emissions resulting from evaporation of a purge stream rather than evaporating a complete salt-containing stream, as in the comparative process of FIG. 1 (stream 24 of FIG. 1). As described in more detail in Example 3, because of this off-set in GHG emissions, the life cycle GHG emissions relative to a gasoline baseline are significantly more favourable than that of the comparative process of FIG. 1.

An example of a process carried out in accordance with embodiments of the invention is described with reference to FIG. 2. As shown in FIG. 2, a cellulosic feedstock slurry prepared from switch grass is subjected to an extractive releasing step, in this case a pretreatment 2 which typically involves the addition of pretreatment chemical and heat to hydrolyze at least a portion of the xylan component of the cellulosic feedstock to release at least xylose, organic acids and salts thereof. The resultant pretreated cellulosic feedstock slurry 4 is then fed to ethanol production and recovery step 6.

In the ethanol production and recovery step 6, the cellulose component of the pretreated cellulosic feedstock slurry is hydrolyzed with cellulase enzymes to produce a hydrolyzed stream comprising glucose and sugars released from xylan including xylose, galactose, mannose, arabinose and glucose. The hydrolyzed stream, comprising glucose and other hexose and pentose sugars, as well as unhydrolyzed, insoluble material comprising lignin, is fed to yeast fermentation to produce a fermented solution containing ethanol. The fermented solution is sent to distillation which produces concentrated ethanol 7 and a still bottoms stream 8.

The still bottoms stream 8 is sent to an SLS 10 to produce a solids stream 12 and an aqueous liquid stream 14 comprising extractives. The liquid stream 14 is then sent to anaerobic digestion unit 16. In this embodiment, the liquid stream 14 fed to anaerobic digestion 16 contains inorganic salts including potassium salts, calcium salts and sodium salts and organic components including organic acids, such as acetic acid and/or acetate, protein, polyols, soluble lignin and lignin derived compounds and unfermented sugars. The anaerobic digestion unit 16 converts the organic components to biogas to produce crude biogas stream 18.

Instead of using the crude biogas stream 18 to fuel a boiler, (e.g., by feeding it to the CHP unit 20 as in the comparative process of FIG. 1), it is fed to a purification unit 34 to remove at least carbon dioxide from the crude biogas 18 to produce a purified biogas stream 36 suitable for pipeline transport. The purified biogas stream 36 is introduced to a pipeline 38 and an amount of methane 39 is withdrawn from the pipeline 38 for use as a transportation or heating fuel or as an intermediate or a feedstock to produce such fuel.

The anaerobic digestion 16 produces an effluent stream 17 that is subjected to a second SLS 22 to produce a salt-containing stream 24. The salt-containing stream 24 is split to form a main stream 24a and a purge stream 40 that is fed to an evaporation unit 26, where the purge stream 40 is evaporated to produce a condensate stream 30 (also referred to herein as an evaporated purge stream 30) and a concentrated salt stream 31. After withdrawing purge stream 40, the salt-containing main stream 24a is recycled to the ethanol production and recovery step 6. For the purposes of the GHG calculations below, it was assumed that 75% of stream 24 was diverted as main stream 24a to recycle to ethanol production and recovery step 6.

In the illustrated embodiment, salt-containing stream 24a comprises potassium salts, calcium salts, sodium salts and in some instances magnesium salts. As mentioned previously, the inorganic salt, particularly potassium salts, such as potassium carbonate can act as buffers and resist changes to the pH upon addition of acid or base during pretreatment. Thus, introducing the inorganic salt-containing stream 24a downstream of pretreatment to the ethanol production and recovery step 6 can avoid this effect, thereby reducing chemical usage.

On the other hand, the condensate stream 30 does not contain inorganic salts and thus may be fed to pretreatment 2 without increasing chemical usage. Furthermore, by implementing the above-described process, the energy requirements for the process are reduced because only a portion of the salt-containing purge stream 40 needs to be evaporated. By contrast, in the process of FIG. 1, the whole salt-containing stream 24 is evaporated, which is comparatively more energy intensive.

An evaporated or concentrated salt-containing stream 31 is then withdrawn from the evaporation unit 26. Advantageously, the concentrated salt-containing stream 31 can be used as a fertilizer or can be recycled in the process to partially neutralize acid.

Example 3: Life Cycle GHG Emissions of Comparative Process Versus an Embodiment of the Invention The life cycle GHG emissions (relative to a gasoline baseline) associated with the comparative process described in FIG. 1 and the inventive process described in FIG. 2 were calculated. For the comparative process of FIG. 1, the life cycle GHG emission savings relative to a gasoline baseline were 66%. However, implementing the process steps of the inventive example described in FIG. 2 increased the GHG savings to 73% relative to a gasoline baseline.

The analysis is described in more detail in Table 3 below. First, the GHG emissions of the comparative process in which crude biogas was fed to a boiler (in this case a combined heat and power unit 20) were quantified. The results are set forth in Part A of Table 3 below. This included quantifying emissions upstream and downstream of the plant, namely process emissions from agriculture, land use changes, feedstock and fuel transport and tailpipe emissions from transport vehicles and then emissions from the fuel production process itself. As described, this process uses biogas to feed a boiler for internal electricity and process heat generation, which has a favourable GHG impact. However, evaporating the complete salt-containing stream 24 (rather than a portion) requires energy which ultimately reduces the amount of electricity that can be generated in CHP 20, and leads to net electricity imports.

Figure 2:
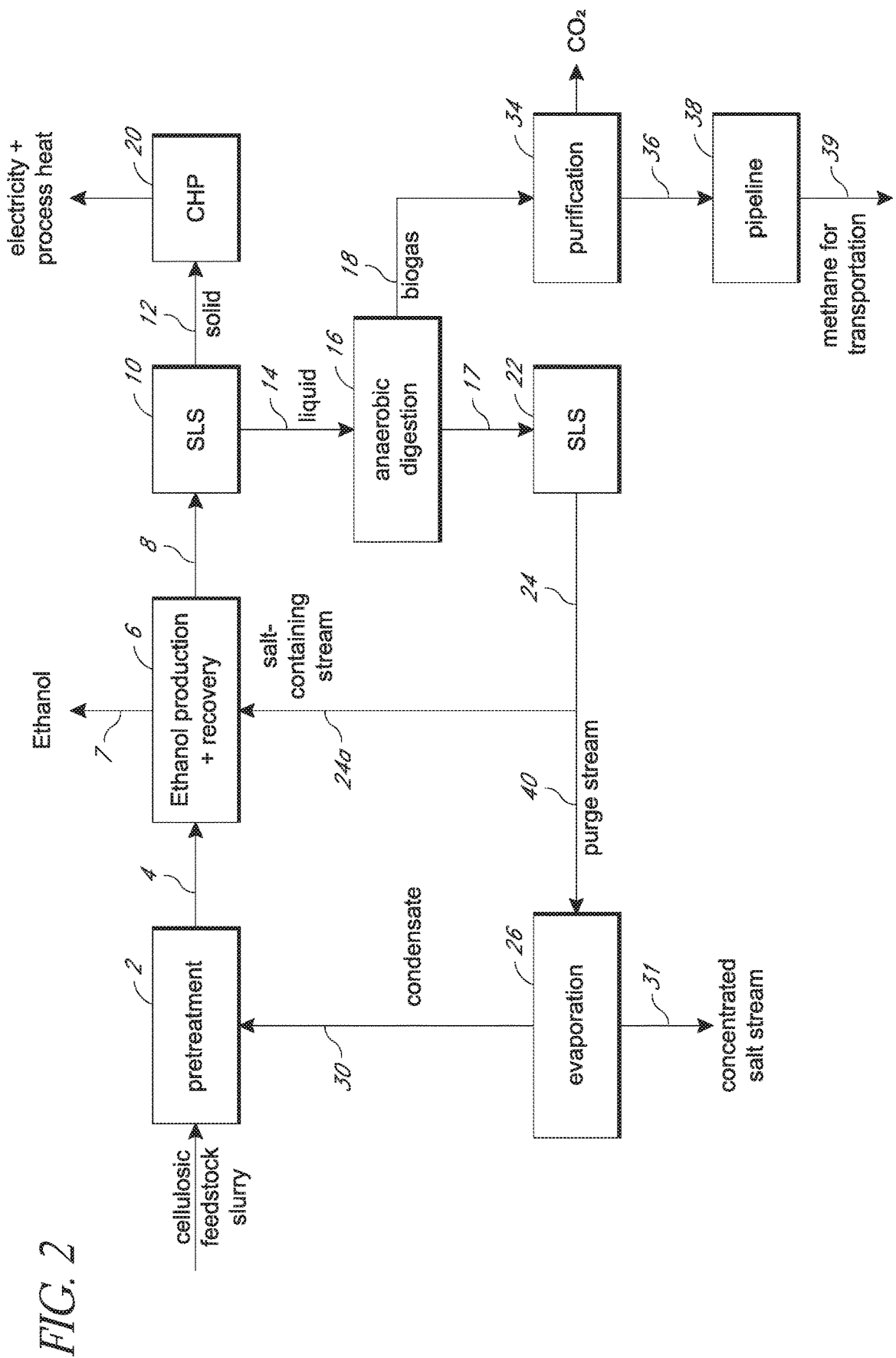
FIG. 2 is a process carried out in accordance with embodiments of the invention comprising a solids-liquid separation upstream of anaerobic digestion to produce a solids stream fed to a thermal process and a liquid stream fed to anaerobic digestion. In the process described a liquid stream originating from an anaerobic digestion is purged and fed to an evaporator and a condensate from evaporation is recycled in the process.

A similar analysis was then conducted for the process of FIG. 2. For the process of FIG. 2, the analysis is described in two parts. First, the negative GHG impact associated with introducing biogas to the pipeline and using a withdrawn amount of methane for transport was determined and factored into the calculations. This lead to a reduction in the life cycle GHG savings relative to a gasoline baseline (only 57% life cycle GHG savings relative to a gasoline baseline). The results are set forth in Part B of Table 3 below.

The second part of the analysis involved additionally factoring in the GHG impact of splitting the salt-containing stream 24 to divert a majority of the evaporator feed (75%) to recycle (i.e., salt-containing stream 24a) and feeding the purge stream 40 (rather than the complete stream 24 as in FIG. 1) to the evaporator 26. Reduced steam use and electricity import due to evaporating only the purge stream 40 portion of the stream 24 resulted in more favourable GHG savings, off-setting the negative impact of adding the biogas 36 to the pipeline 38 and using withdrawn methane as transportation fuel. By implementing this latter step, the life cycle GHG savings relative to a gasoline baseline increased to 73%. The results are set forth in Part C of Table 3 below. The calculations were based in part on an NREL 2011 study, Humbird et al., NREL/TP-5100-47764, May 2011.

TABLE 3

GHG emissions associated with comparative process versus an embodiment of the invention

| | UNITS | GHG MEASURE |
|---|---|---|
| PART A. COMPARATIVE PROCESS WITH BIOGAS TO BOILER (FIG. 1) | | |
| a. Process emissions agriculture, land use changes, feedstock and fuel transport and tailpipe emissions | tons $CO_2$eq/yr | 108,031 |
| b. Process emissions from ethanol production | tons $CO_2$eq/yr | 49,889 |
| c. Total emissions (108,031 + 49,889) | tons $CO_2$eq/yr | 157,920 |
| d. Fuel production (ethanol 7) | MMBTU/yr | 4,697,000 |
| e. Emissions of fuel | g$CO_2$eq/MMBTU | 33,621 |
| Percent GHG reduction relative to gasoline baseline | | 66% |
| PART B. BIOGAS ADDITION TO PIPELINE FOR TRANSPORT (FIG. 2) | | |
| a. Process emissions agriculture, land use changes, feedstock and fuel transport and tailpipe emissions | tons $CO_2$eq/yr | 108,031 |
| Negative impact of adding biogas to pipeline (increased electricity imports) | tons $CO_2$eq/yr | 123,230 |
| b. Process emissions from ethanol production (baseline of 49,889 + 123,230 from higher electricity imports) | tons $CO_2$eq/yr | 173,119 |
| c. Total emissions (108,031 + 173,119) | tons $CO_2$eq/yr | 281,150 |
| d. Fuel production (ethanol 7 + biogas 39) | MMBTU/yr | 6,678,140 |
| e. Emissions of fuel | g$CO_2$eq/MMBTU | 42,100 |
| Percent GHG reduction relative to gasoline baseline | | 57% |
| PART C. BIOGAS ADDITION TO PIPELINE + RECYCLE OF EVAPORATED PURGE STREAM (FIG. 2) | | |
| a. Process emissions agriculture, land use changes, feedstock and fuel transport and tailpipe emissions | tons $CO_2$eq/yr | 108,031 |
| b. Process emissions from fuel production | tons $CO_2$eq/yr | 67,658 |
| c. Total emissions | tons $CO_2$eq/yr | 175,689 |
| d. Fuel production emissions (ethanol 7 + biogas 39) | MMBTU/yr | 6,678,140 |
| e. Emissions of fuel | g$CO_2$eq/MMBTU | 26,308 |
| % GHG reduction relative to gasoline baseline | | 73% |

As shown in Part B of Table 3 above, by contrast to using biogas internally in the process for heat and electricity (FIG. 1), the pipeline transport and use of methane withdrawn from the pipeline for transportation fuel (FIG. 2) increases the process GHG emissions to 173,119 tons $CO_2$eq/yr, an increase of 123,230 tons $CO_2$eq/yr over the baseline of 49,889 tons $CO_2$eq/yr in Part A (comparative process) of Table 3. This increase is due to the additional electricity that must be imported because the electricity generation from CHP 20 is reduced when biogas fuel is removed. The total emissions of the process of FIG. 1 are 157,920 tons $CO_2$eq/yr, whereas the emissions after biogas removal from CHP 20 increase to 281,150 tons $CO_2$eq/yr. However, because the total fuel production of the process of FIG. 2 is higher (6,678,140 MMBTU/yr vs. 4,697,000 of FIG. 1), the net result is a decrease in GHG savings from 66% (FIG. 1) to 57% (FIG. 2 without purge and evaporation).

Comparing Part B with Part C of Table 3 shows that process emissions from fuel production were 173,119 tons $CO_2$eq/yr for the process with only biogas export, but were reduced to 67,658 tons $CO_2$eq/yr when the evaporation of the purge stream with recycle was included in the emissions calculation (Part C). This reduction in emissions relative to the comparative process contributed to the favourable emissions of 73% relative to the gasoline baseline. That is, despite the negative GHG impact associated with using methane sourced from the process as transportation fuel, the overall, net GHG emissions, quantified as life cycle GHG emissions relative to a gasoline baseline, were actually found to be improved relative to a similar process in which biogas is used for internal heat and power generation.

As a result of its favourable life cycle GHG emissions, the above-described embodiment of FIG. 2 incentivizes the use of methane sourced from cellulosic feedstock for use in the transportation sector rather than simply for on-site energy use in a plant. Thus, implementation of the example set out in FIG. 2 may promote the more widespread use of this biofuel in the transportation sector, which in turn improves the prospects for increased biofuel commercialization.

Although evaporation of a purge stream 40 is described above with reference to FIG. 2, the purge stream 40 can be subjected to other water removal steps instead of, or in addition to, evaporation (not illustrated in FIG. 2). Examples include concentration with membrane, freeze crystallization and/or other processing techniques. Energy savings are potentially realized because similar to the evaporation described above, only a portion of stream 24 is subjected to the water removal or other processing. Further, recovery of salt from the concentrated salt stream 31 to produce fertilizer can displace fertilizer made from non-renewable sources, which could also reduce GHG emissions.

Figure 3:
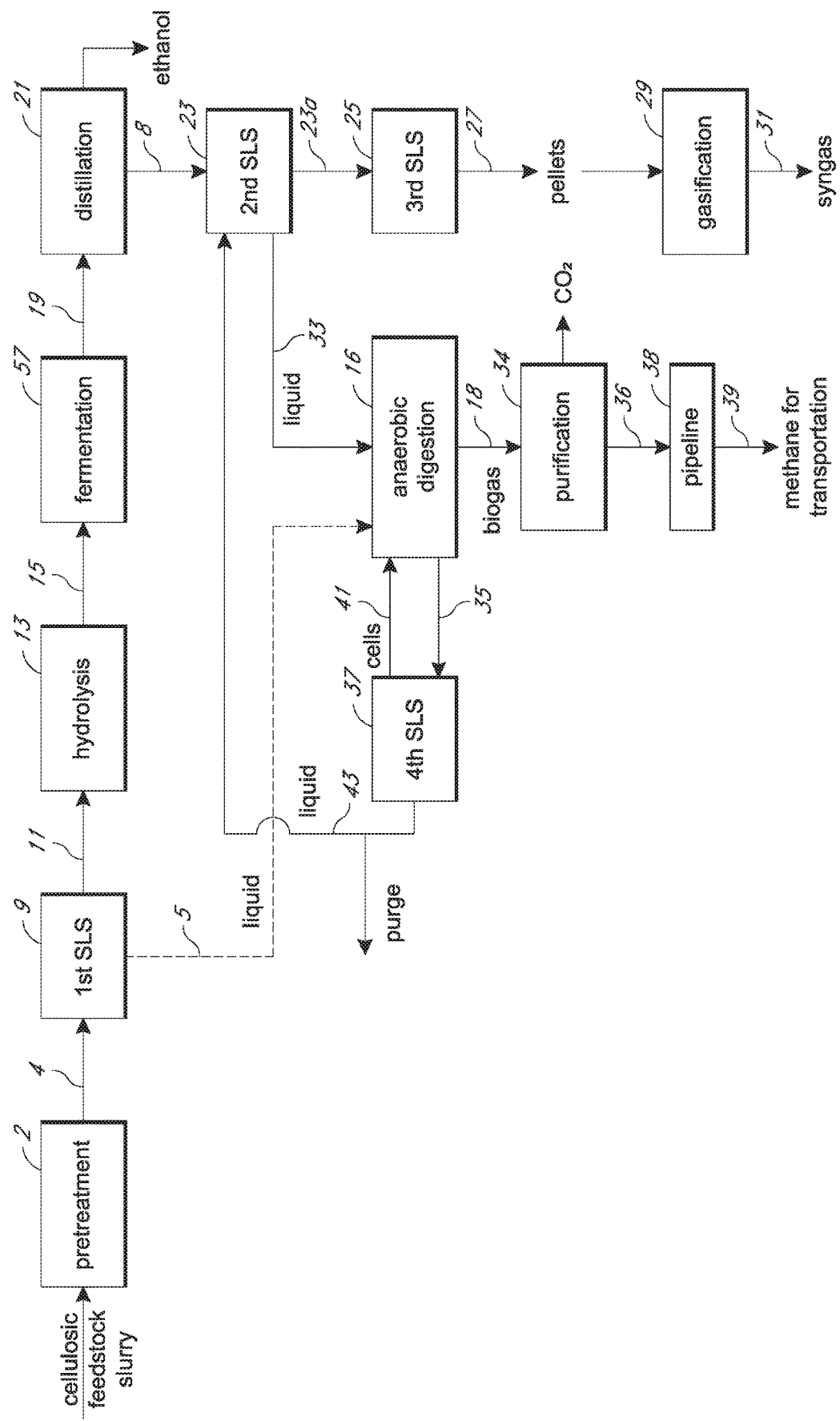
FIG. 3 is a process carried out in accordance with embodiments of the invention in which a still bottoms stream is subjected to solids-liquid separation to produce a solids stream that is further processed to pellets in a subsequent solids-liquid separation and wherein liquid from the solids-liquid separation is fed to anaerobic digestion to produce biogas.

Example 4: Description of Further Embodiments Employing Solids-Liquid Separation and Water Recycle An example of a further process configuration carried out in accordance with embodiments of the invention is described with reference to FIG. 3. As shown in FIG. 3, a cellulosic feedstock slurry prepared from switch grass is subjected to an extractive releasing step, in this case a pretreatment 2 which typically involves the addition of pretreatment chemical and heat to hydrolyze at least a portion of the xylan component of the cellulosic feedstock to release at least xylose, organic acids and salts thereof. The resultant pretreated cellulosic feedstock slurry 4 is then fed to a first solids-liquid separation (SLS) 9 to produce pretreated solids stream 11. The pretreated solids stream 11 is fed to hydrolysis 13 while the liquid stream 5 comprising at least acetic acid, acetate or a combination thereof is fed to anaerobic digestion 16. The introduction of organic acids to anaerobic digestion has the benefit of potentially increasing biogas yield. In the hydrolysis 13, the cellulose component of the pretreated cellulosic feedstock is hydrolyzed with cellulase enzymes to produce a hydrolyzed stream 15 comprising at least glucose. The hydrolyzed stream 15, comprising at least glucose, as well as unhydrolyzed, insoluble material comprising lignin, is fed to yeast fermentation 57 to produce a fermented solution 19 containing ethanol. The fermented solution 19 is sent to distillation 21 which produces concentrated ethanol and a still bottoms stream 8.

The still bottoms stream 8 is sent to a second SLS 23 to produce a liquid stream 33 and a solids stream 23a that is subsequently fed to a third SLS 25 where additional water is removed to produce pellets 27. The pellets 27 are gasified in gasification unit 29 to produce syngas 31. The liquid stream 33 from the second SLS 23 is then sent to anaerobic digestion unit 16. An effluent stream 35 from anaerobic digestion unit 16 comprising microorganisms is sent to a fourth SLS 37 where the microorganisms are separated to produce a slurry comprising microorganisms 41 and a liquid stream 43. The liquid stream 43, which is substantially free of microorganisms, is recycled to second SLS 23.

The anaerobic digestion unit 16 converts the organic extractive components of liquid stream 33 to biogas to produce crude biogas stream 18. The crude biogas stream 18 is fed to a purification unit 34 to remove at least carbon dioxide from the crude biogas 18 to produce a purified biogas stream 36 suitable for pipeline transport. The purified biogas stream 36 is introduced to a pipeline 38 and an amount of methane 39 is withdrawn from the pipeline 38 for use as a transportation or heating fuel or as an intermediate or a feedstock to produce another fuel.

Figure 4:
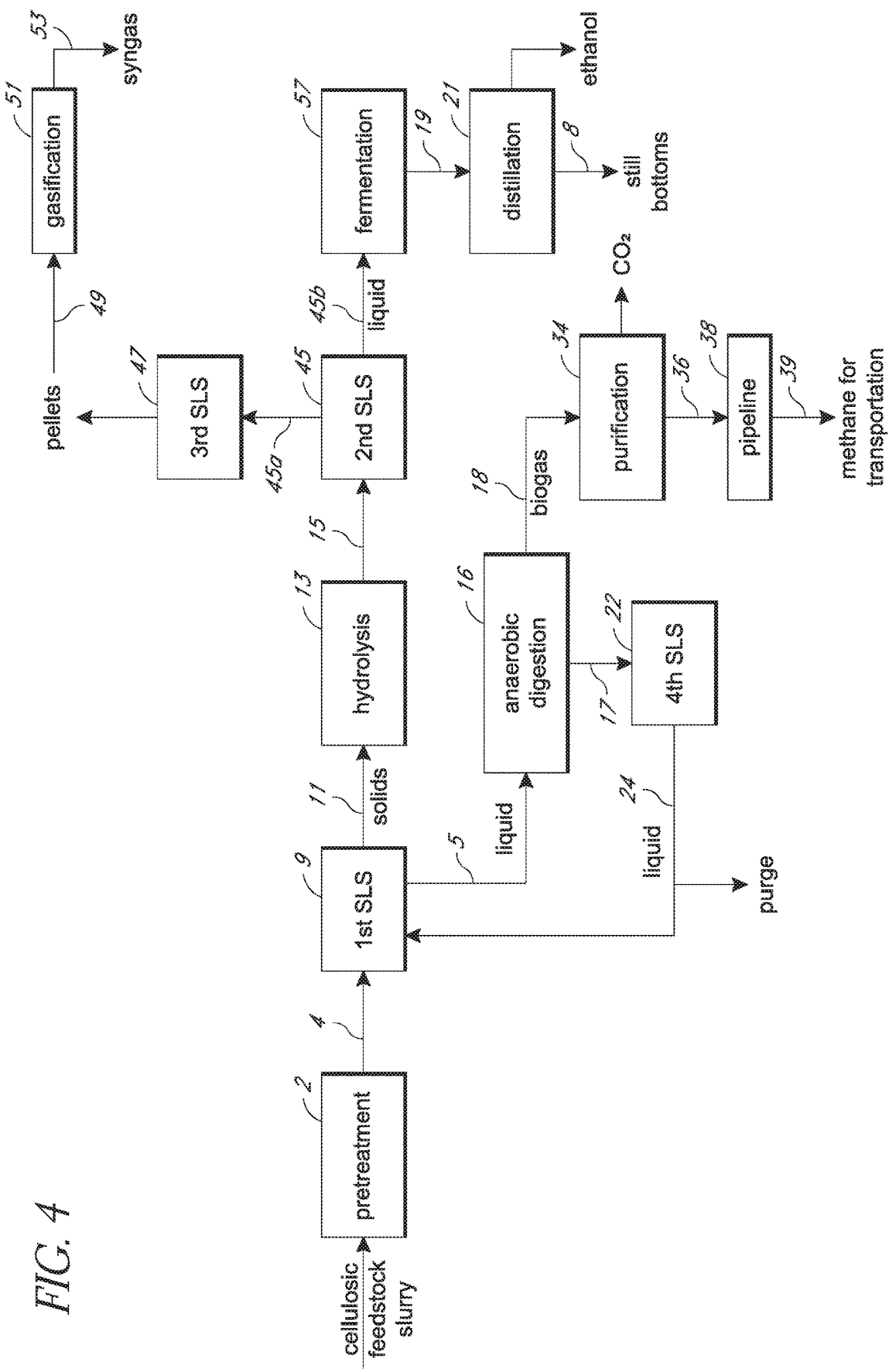
FIG. 4 is a process carried out in accordance with embodiments of the invention in which a pretreated feedstock stream is subjected to a solids-liquid separation to produce a liquid stream that is fed to anaerobic digestion and solids stream that is further hydrolyzed with cellulase enzymes to produce a hydrolysate comprising glucose. The hydrolysate stream resulting from cellulose hydrolysis of a pretreated feedstock is subjected to solids-liquid separation to produce a solids stream that is further processed in a subsequent solids-liquid separation to produce pellets.

An example of yet a further process configuration carried out in accordance with embodiments of the invention is described with reference to FIG. 4. As shown in FIG. 4, a cellulosic feedstock slurry prepared from switch grass is subjected to an extractive releasing step, in this case a pretreatment 2 which typically involves the addition of pretreatment chemical and heat to hydrolyze at least a portion of the xylan component of the cellulosic feedstock to release at least xylose, organic acids and salts thereof. The resultant pretreated cellulosic feedstock slurry 4 is then fed to a first SLS 9 to produce pretreated solids stream 11 and a liquid stream 5. The pretreated solids stream 11 is fed to hydrolysis 13, while the liquid stream 5 comprising at least acetic acid, acetate or a combination thereof, and optionally sugar released from xylan, is fed to anaerobic digestion 16. In the hydrolysis 13, the cellulose component of the pretreated cellulosic feedstock is hydrolyzed with cellulase enzymes to produce a hydrolyzed stream 15. The hydrolyzed stream 15, comprising glucose, as well as unhydrolyzed, insoluble material comprising lignin, is fed to a second SLS 45 to produce a solids stream 45a and a liquid stream 45b. The solids stream 45a is sent to a third SLS 47 to remove further water to produce pellets 49. The pellets 49 are then subjected to gasification 51 to produce syngas 53. Syngas 53 is used as a fuel itself or to make another fuel or fuel intermediate.

The liquid stream 45b from the second SLS 45 is fed to yeast fermentation 57 to produce a fermented solution 19 containing ethanol. The fermented solution 19 is sent to distillation 21 which produces concentrated ethanol and a still bottoms stream 8.

As described previously, the liquid stream 5 from first SLS 9 is fed to anaerobic digestion unit 16 which converts the organic extractive components of liquid stream 5 to biogas to produce crude biogas stream 18. The crude biogas stream 18 is fed to a purification unit 34 to remove at least carbon dioxide from the crude biogas 18 to produce a purified biogas stream 36 suitable for pipeline transport. The purified biogas stream 36 is introduced to a pipeline 38 and an amount of methane 39 is withdrawn from the pipeline 38 for use as a transportation or heating fuel or as an intermediate or a feedstock to produce such fuel.

The process of FIG. 4 also implements recycle of liquid originating from the anaerobic digestion unit 16. An effluent stream 17 from the anaerobic digestion unit 16 is fed to fourth SLS 22. A liquid stream 24 (optionally purged) from the fourth SLS 22 is introduced to the first SLS 9 to reduce water usage in the process.

An example of yet a further process configuration carried out in accordance with embodiments of the invention is described with reference to FIG. 5. In this example, stages upstream of anaerobic digestion 16 are conducted under low water conditions. For example, pretreatment 2 and cellulose hydrolysis may be carried out at a consistency ranging from 12 wt % to 30 wt % undissolved solids (w/w), which is higher than conventional, i.e., typically between 5 and 12 wt % (w/w)). There are numerous advantages to operating at higher than conventional undissolved solids consistencies. For example, during chemical pretreatment, the lower water content in the incoming slurry requires less steam for the heat-up, as well as chemical. During enzymatic hydrolysis, the volumetric efficiency of the process is improved at high solids content. Furthermore, at high solids content, the hydrolysis product will contain a high concentration of fermentable sugars, which improves productivity.

However, the introduction of concentrated streams to an anaerobic digester having a correspondingly high concentration of extractives can be toxic to the microorganisms and reduce the efficiency of the process. By introducing a liquid stream to a stream that feeds the digester (e.g., liquid stream 14 of FIG. 5), the concentration of toxic extractives is reduced, and thereby anaerobic digestion can potentially be made operational without the excess use of water for dilution. Recycle may also result in an effluent stream from the digester with a higher salt concentration than could otherwise be achieved, which can reduce the cost of subsequent processing to remove water, such as evaporation or reverse osmosis to dispose of such effluent streams.

Figure 5:
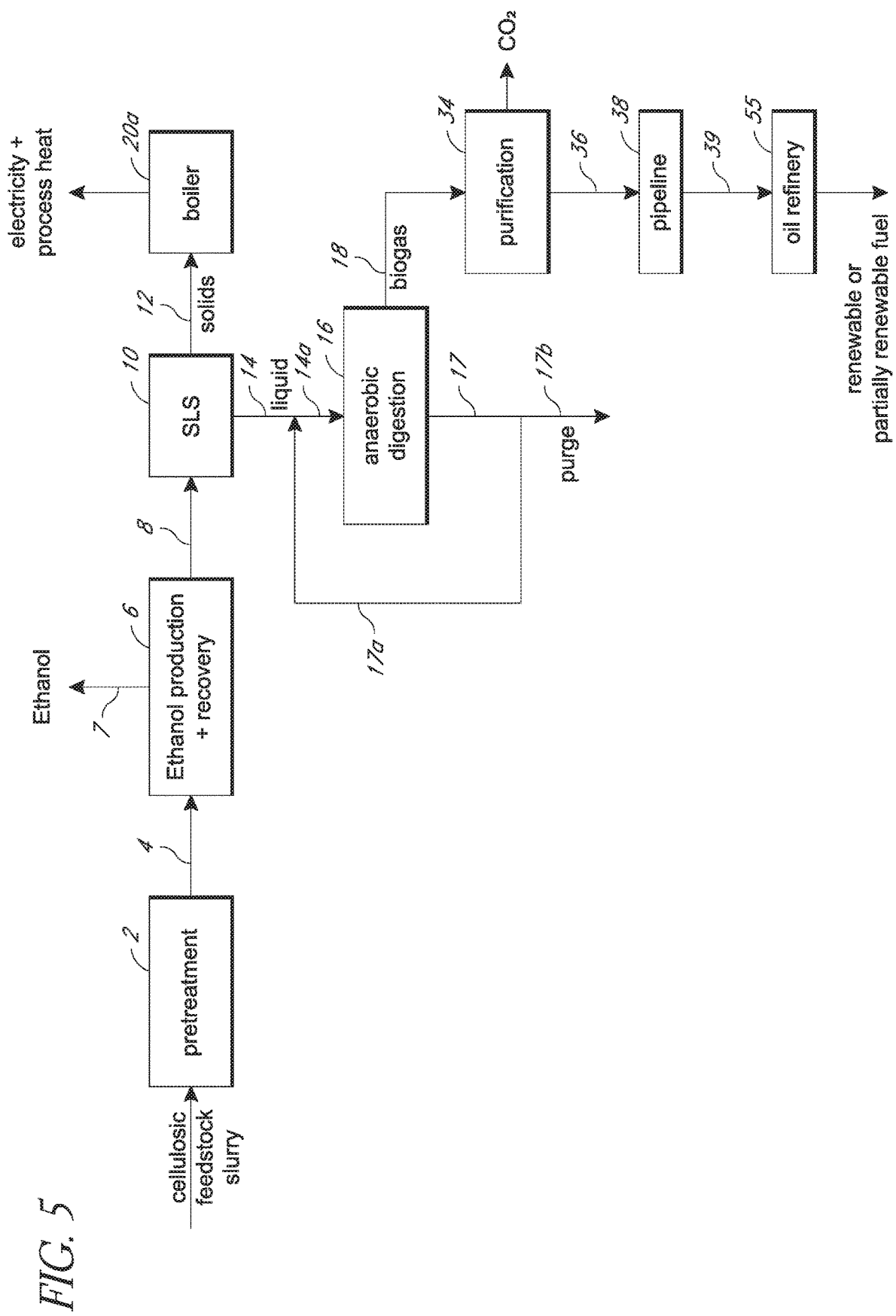
FIG. 5 is a process carried out in accordance with embodiments of the invention in which a still bottoms stream is subjected to solids-liquid separation to produce a solids stream that is fed to a boiler and wherein liquid from the solids-liquid separation is fed to an anaerobic digester to produce biogas. The process described shows re-circulation of an effluent stream from the anaerobic digester to a stream that feeds anaerobic digester.

As shown in FIG. 5, a cellulosic feedstock slurry prepared from switch grass is subjected to an extractive releasing step, in this case a pretreatment 2 which typically involves the addition of pretreatment chemical and heat to hydrolyze at least a portion of the xylan component of the cellulosic feedstock to release at least xylose, organic acids and salts thereof. The resultant pretreated cellulosic feedstock slurry 4 is then fed to ethanol production and recovery step 6, which produces ethanol 7.

In the ethanol production and recovery step 6, the cellulose component of the pretreated cellulosic feedstock slurry is hydrolyzed with cellulase enzymes to produce a hydrolyzed stream comprising glucose and sugars released from xylan including xylose, galactose, mannose, arabinose and glucose. The hydrolyzed stream, comprising glucose and other hexose and pentose sugars, as well as unhydrolyzed, insoluble material comprising lignin, is fed to yeast fermentation to produce a fermented solution containing ethanol. The fermented solution is sent to distillation which produces concentrated ethanol 7 and a still bottoms stream 8.

The still bottoms stream 8 is fed to an SLS 10 to produce a solids stream 12 and an aqueous liquid stream 14 comprising extractives. The solids stream 12 is sent to a boiler 20a to generate electricity and/or process heat. The liquid stream 14 is then sent to anaerobic digestion unit 16. In this embodiment, the liquid stream 14 fed to anaerobic digestion 16 contains a high concentration of extractives such as one or more of inorganic salts including potassium salts, calcium salts and sodium salts as well as organic components including organic acids, such as acetic acid and/or acetate, protein, polyols, soluble lignin and lignin derived compounds and unfermented sugars. A potassium-containing main stream 17a, described further below, is added to the liquid stream 14, which dilutes the extractives. The anaerobic digestion unit 16 converts the organic components to biogas to produce crude biogas stream 18.

The crude biogas stream 18 is fed to a purification unit 34 to remove at least carbon dioxide from the crude biogas 18 to produce a purified biogas stream 36 suitable for pipeline transport. The purified biogas stream 36 is introduced to a pipeline 38 and an amount of methane 39 is withdrawn from the pipeline 38 for use in an oil refinery 55. In the oil refinery 55, the methane 39 is converted to renewable hydrogen, which in turn is used in a process to produce a renewable or partially renewable liquid transportation or heating fuel. For example, the renewable hydrogen may be combined with a crude oil derived liquid hydrocarbon so that it becomes incorporated into the hydrocarbon and ultimately becomes part of the liquid transportation or heating fuel that is the product of the fuel production facility. (See, e.g., U.S. Pat. Nos. 8,753,843, 8,658,026 and 8,945,373).

The anaerobic digestion unit 16 produces an effluent stream 17 containing salt, in this embodiment potassium salt. The effluent stream 17 is split to form a potassium-containing main stream 17a and a purge stream 17b. After withdrawing purge stream 17b, the potassium-containing main stream 17a is combined with the liquid stream 14 that feeds the anaerobic digestion unit 16. Addition of the potassium-containing main stream 17a to liquid stream 14 results in a diluted combined stream 14a. The diluted combined stream 14a fed to the digestion unit 16 has a reduced concentration of extractives, thereby potentially improving the efficiency of the anaerobic digestion by reducing the concentration of toxic extractives. In turn, the purge stream 17b can be used to produce a product, such as a potassium fertilizer, subjected to aerobic digestion and disposed of, introduced underground or used to neutralize an acidic stream in the process.

Those of ordinary skill will understand that the embodiments and examples discussed herein are non-limiting, and accordingly other configurations or variations of the above configurations, may be utilized in conformity with the present invention.

The invention claimed is:

1. A process for producing a transportation or heating fuel comprising the steps of:
   (i) treating a cellulosic feedstock in one or more processing steps that release extractives from the feedstock, said extractives comprising acetic acid, acetate, or a combination thereof;
   (ii) conducting a solids-liquid separation on a process stream comprising the extractives and solids comprising insoluble components, thereby producing an aqueous stream comprising the extractives and a solids stream comprising insoluble components;
   (iii) feeding an aqueous stream comprising one or more of the extractives or a portion of said aqueous stream to an anaerobic digester to produce crude biogas and optionally removing at least a portion of one or more impurities from the crude biogas;
   (iv) carrying out or causing one or more parties to carry out a process comprising (a) gasifying a solids stream comprising the insoluble components to produce syngas, and (b) reacting the syngas to produce a fuel or fuel component;
   (v) providing biogas from step (iii) or one or more products derived therefrom for use as a transportation or heating fuel; and
   (vi) generating or causing generation of a renewable fuel credit.

2. The process of claim 1, wherein the cellulosic feedstock is straw, stover, or an energy crop.

3. The process of claim 1, comprising obtaining a liquid stream from the anaerobic digester and recirculating the liquid stream or a portion thereof to the anaerobic digester or to a stage upstream of the anaerobic digester.

4. The process of claim 1, comprising:
(a) obtaining a liquid stream from the anaerobic digester and introducing the liquid stream or a portion thereof to the anaerobic digester or to a stage upstream of the anaerobic digester; and
(b) conducting a second solids-liquid separation on the solids stream comprising the insoluble components or a stream derived therefrom to produce a second aqueous stream and introducing the second aqueous stream or a portion thereof to the digester or to a stage upstream of the digester.

5. The process of claim 1, wherein the aqueous stream comprising one or more of the extractives or the portion of said aqueous stream further comprises sulfur and wherein said process further comprises:
(a) converting the sulfur or a portion thereof to gaseous hydrogen sulfide in said anaerobic digester;
(b) treating the gaseous hydrogen sulfide to produce elemental sulfur or an oxide of sulfur;
(c) recovering an acid comprising sulfuric acid, sulfurous acid, sulfur dioxide or a combination thereof from the elemental sulfur or oxide of sulfur; and
(d) using the recovered acid in the process as a catalyst or for neutralizing alkali.

6. The process of claim 1, wherein gasifying the solids stream comprising the insoluble components comprises gasifying densified solids.

7. The process of claim 1, wherein reacting the syngas to produce a fuel or fuel component comprises producing methane.

8. The process of claim 1, wherein reacting the syngas to produce a fuel or fuel component comprises producing hydrogen.

9. The process of claim 1, wherein reacting the syngas to produce a fuel or fuel component comprises producing ammonia.

10. The process of claim 1, wherein reacting the syngas to produce a fuel or fuel component comprises producing dimethyl ether.

11. The process of claim 1, wherein reacting the syngas to produce a fuel or fuel component comprises producing methanol.

12. The process of claim 1, wherein reacting the syngas to produce a fuel or fuel component comprises producing ethanol.

13. The process of claim 1, wherein reacting the syngas to produce a fuel or fuel component comprises producing liquid hydrocarbons.

14. The process of claim 1, wherein reacting the syngas to produce a fuel or fuel component comprises reacting the syngas in a methanation reaction.

15. The process of claim 1, wherein reacting the syngas to produce a fuel or fuel component comprises reacting the syngas in a Fischer Tropsch process.

16. The process of claim 1, wherein reacting the syngas to produce a fuel or fuel component comprises using hydrogen from the syngas to hydrogenate a crude oil derived liquid hydrocarbon.

* * * * *